(12) United States Patent
Rodriguez et al.

(10) Patent No.: US 8,334,135 B2
(45) Date of Patent: Dec. 18, 2012

(54) STEM CELLS FROM ADIPOSE TISSUE, AND DIFFERENTIATED CELLS FROM SAID CELLS

(75) Inventors: Anne-Marie Rodriguez, Nice (FR); Christian Dani, Nice (FR); Gerard Ailhaud, Gonfaron (FR)

(73) Assignee: Yves Saint Laurent Parfums, Neuilly sur Seine (FR)

( * ) Notice: Subject to any disclaimer, the term of this patent is extended or adjusted under 35 U.S.C. 154(b) by 403 days.

(21) Appl. No.: 10/632,581

(22) Filed: Jul. 31, 2003

(65) Prior Publication Data

US 2004/0229351 A1 Nov. 18, 2004

(30) Foreign Application Priority Data

Jul. 31, 2002 (FR) .................................. 02 09799
Feb. 28, 2003 (FR) .................................. 03 02657

(51) Int. Cl.
*C12N 5/00* (2006.01)
*C12N 5/02* (2006.01)

(52) U.S. Cl. ....................................................... 435/325

(58) Field of Classification Search ........................ None
See application file for complete search history.

(56) References Cited

U.S. PATENT DOCUMENTS

| 5,589,483 | A | * | 12/1996 | West ............................... | 514/310 |
| 5,733,542 | A | * | 3/1998 | Haynesworth et al. ........ | 424/93.7 |
| 2003/0082152 | A1 | * | 5/2003 | Hedrick et al. ............. | 424/93.21 |
| 2004/0033214 | A1 | * | 2/2004 | Young et al. ................. | 424/93.7 |

FOREIGN PATENT DOCUMENTS

| WO | WO 00/53795 | * | 9/2000 |
| WO | WO 0053795 | | 9/2000 |
| WO | WO 0111011 | | 2/2002 |

OTHER PUBLICATIONS

Pittenger et al., 1999, Science, 284: 143-147.*
Zuk et al., 2001, Tissue Engineering, 7: 211-228.*
Katz AJ. Mesenchymal cell culture: adipose tissue. In Atala A, Lanza RP, eds. Methods of Tissue Engineering. Academic Press, NY: 2002: 277-286.*
Akanbi et al., 1994, J. Anim. Sci., 72: 2828-2835.*
Wagner et al., 2004, Arterioscler. Thomb. Vasc. Biol., 24: 715-720.*
Kataoka et al., 2003, Blood, 102: 3224-3231.*
Tremain et al., 2001, Stem Cells, 19: 408-418.*
Djian et al., 1983, J. Clin. Invest. 72: 1200-1208.*
Young et al., 1996, Blood, 87: 545-556.*
Didinksy et al., 1981, Journal of Cellular Physiology, 109: 171-179.*
Martin et al., 1997, Endocrinology, 138: 4456-446.*
Zheng et al., 2006, Biotechnol. Prog. 22: 1294-1300.*
Lee R.H. et al., Multipotent Mesenchymal Stem Cells from Adult Human Adipose Tissue and Femur Bone Marrow, 2002 FASEB Journal, vol. 16, pp. A425 (Exhibit 4).
Zuk Patricia et al., Multilineage Cells from Human Adipose Tissue: Implications for Cell-Based Therapies, 2001 Tissue Engineering, vol. 7, pp. 211-228 (Exhibit 5).
Zuk Patricia et al., Human Adipose Tissue is a Source of Multipotent Stem Cells, (2002), Molecular Biology of the Cell, vol. 13(12) pp. 4279-4295 (Exhibit 6).
U.S. Appl. No. 60/162,462, filed Oct. 29, 1999, Katz et al.
Kang, M.K. et al., (1998) "Replicative Senescence of Normal Human Oral Keratinocytes is Associated With the Loss of Telomerase Activity Without Shortening of Telomeres", Cell Growth and Differentiation, 9:85-95.
Zimmerman, S. et al., (2003) "Lack of Telomerase Activity in Human Mesenchymal Stem Cells", Leukemia 17(6):1146-1149.
Gronthos S., et al., "Surface Protein Characterization of Human Adipose Tissue-Derived Stromal Cells", Journal of Cellular Physiology 189 :54-63 (2001).
Katz et al., "Cell Surface and Transcriptional Characterization of Human Adipose-Derived Adherent Stromal (hADAS) Cells", Stem cells, 23, 412-423 (2005).
Strem BM, et al., "Multipotential Differentiation of Adipose Tissue-Derived Stem Cells", Keio J Med, 54(3), 132-141 (2005).
Wagner et al., "Comparative Characteristics of Mesenchymal Stem Cells From Human Bone Marrow, Adipose Tissue, and Umbilical Cord Blood", Experimental Hematology, 33, 1402-1416 (2005).
Bernardo M.E. et al., "Human Bone Marrow-Derived Mesenchymal Stem Cells Do Not Undergo Transformation After Long-Term in Vitro Culture and Do Not Exhibit Telomere Maintenance Mechanisms", Cancer Research, 67; (19), 9142-9149 (2007).

* cited by examiner

*Primary Examiner* — Joanne Hama

(74) *Attorney, Agent, or Firm* — John P. White; Cooper & Dunham LLP

(57) ABSTRACT

The invention concerns adult multipotent human stem cells, characterized in that they have:
  i) significant telomerase activity,
  ii) an HLA Class I negative phenotype,
  iii) a normal karyotype,
  iv) a capacity to become quiescent,
  v) a capacity for self-renewal preserved for at least 130 population doublings.

10 Claims, 32 Drawing Sheets

CS T1　　　　　　　CST7　　　　　　　CA T5 hPPARγ haP2 hOC

Primo2 CA T32

STEM CELLS FROM ADIPOSE TISSUE, AND DIFFERENTIATED CELLS FROM SAID CELLS

Figure 1:
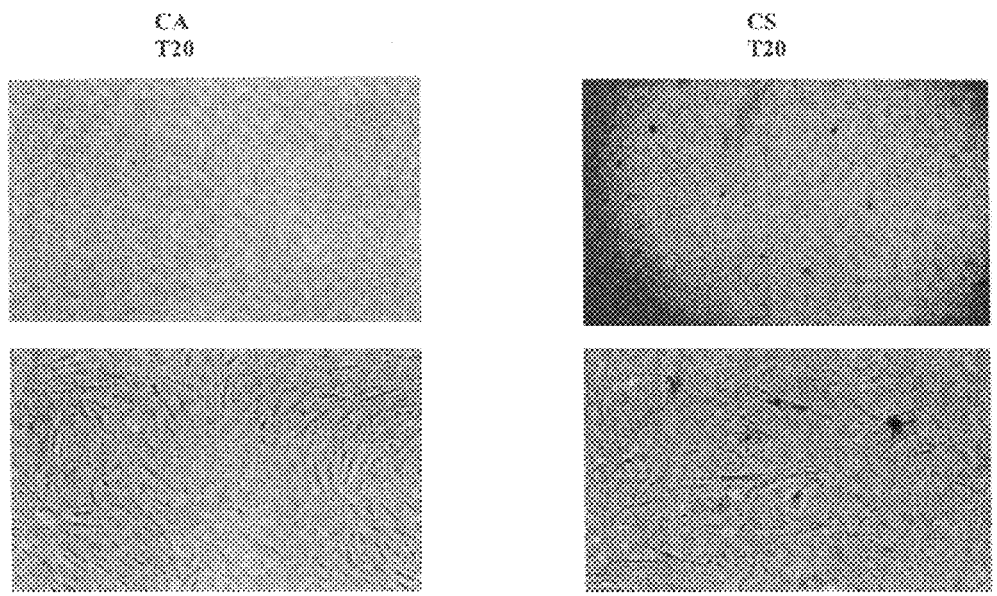

The present invention relates to multipotent human stem cells that can be isolated from human adipose tissue and to the use of said cells in therapy and cosmetology. The invention also concerns a method for isolating said stem cells from adult human adipose tissue and to a method for differentiating them into cells of endodermal or ectodermal or mesodermal origin. Finally, the invention relates to screening methods for identifying agents that are capable of exerting an effect either on cell differentiation or on the function of differentiated cells.

The presence of adult multipotent "stem" cells has been demonstrated in a large number of tissues, for example the bone marrow, blood, liver, muscle, the nervous system, and in adipose tissue. Adult "stem" cells, which in theory are capable of infinite self-renewal, have great cell plasticity, i.e. the ability to differentiate into tissues other than those for which it was believed they were destined. The properties of said cells, which are similar to those of embryonic stem cells (ES), open up considerable therapeutic perspectives especially as their use does not pose the problems of compatibility and ethics, encountered with ES cells.

Unfortunately, their medical application (transplantation) is currently extremely limited for two main reasons:

firstly, it is very difficult to isolate said cells. Indeed Stem cells are very rare in an organism and very little is currently known about them, in particular at a molecular level, rendering direct purification impossible. There is a method for enriching multipotent cells (a population known as "SP" for "side population") based on the capacity to exclude a vital stain (Goodell M A et al. (1996), J Exp Med, vol 83, 1797-1806; Zhou S et al. (2001) Nature Medecine, vol 7, 1028-1034). Other methods involve positive or negative selection, based on the presence or absence of cell markers. As an example, International patent application WO 01/11011 describes the depletion of bone marrow cells of CD45+ glycophorin A+ cells followed by culturing CD45−/GlyA− cells in the presence of growth factors. A similar method has been described by Reyes et al (Blood, November 2001, vol. 98, no 9, 2615-2625).

secondly, prior amplification of said cells in the undifferentiated state in vitro poses a major problem.

While many investigators have successfully demonstrated the presence of multipotent human cells in a large number of tissues, no-one has been able to maintain these cells in vitro in the undifferentiated state beyond 50 to 80 population doublings. Self-renewal capacity is a doubly important indicator: first, because of the very limited number of stem cells naturally present in adult tissue, a quantity of stem cells sufficient for therapeutic use can only be obtained if they can be multiplied in vitro while preserving their original characteristics. Second, the self-renewal capacity is closely related to the very definition of a true stem cell (which is immortal) and thus can be indirectly correlated with extended cell plasticity. Thus, it is highly-desirable to be able to isolate multipotent cells with a self-renewal capacity that is conserved beyond 100 population doublings.

International patent application WO 01/11011 (Furcht, Verfaillie and Reyes) describes human multipotent cells isolated from bone marrow. Said cells have a normal caryotype, a negative HLA class I phenotype and can be maintained in culture in vitro up to 40 population doublings. However, some rare cells can reach 70 population doublings. The authors indicate that these cells can differentiate into cells of the mesodermal lineage, for example into osteoblasts, chondroblasts, adipocytes and myocytes, and also into cells of the ectodermal lineage and of the endodermal lineage. Said cells, however, are capable of a limited number of divisions, and so the authors suggest that, to allow the production of a large quantity of cells, a heterologous gene coding for telomerase should be introduced. The heterologous gene must be excised before using in transplantation. This reversible immortalization technique remains highly controversial, however. There is in fact a risk of malignant transformation of cells when an exogenous telomerase activity is introduced at a level of expression that is non-physiological and not controlled by the cell (Wong Jing et al., Nature, 405, June 2000, 755-756). Similar studies have also been described by Reyes et al (Blood, November 2001, vol. 98, no 9, 2615-2625).

Jiang et al (Nature, Advance Online Publication 20 Jun. 2002, doi:10.1098/nature00870) describe the production of multipotent mouse and rat cells which can be maintained in culture in vitro beyond 100 population doublings. The authors also make reference to a human multipotent population which could be maintained in vitro beyond 80 population doublings. However, no supplemental information is given on the subject of these human cells.

Qu-Petersen et al (J. Cell Biol. 157, 5, 2002, 851-864) report the production of multipotent murine cells from muscle tissue. Said cells, termed "MDSC" cells ("Muscle Derived Stem Cells"), have a normal caryotype and have a self-renewal capacity while retaining their multipotentiality for about 30 population doublings. They can differentiate into cells from different lineages. However, the multipotent character disappears beyond 40 population doublings, at which stage the cells become senescent and die. This work strongly suggests that said multipotent cells display immunoprivileged behavior. Indeed, injection of said cells into the muscles of dystrophic mice which are immunologically different from those from which the MDSC cells are derived, results in substantial muscle regeneration even in the absence of immunosuppressive substances of the cyclosporine type. Surprisingly, the authors observed that the transplantation did not cause infiltration of tissue by $CD4^+$ and $CD8^+$ lymphocytes of the grafted mouse. This tolerance is at least in part explained by the negative MHC class I phenotype of the MDSC cells. This work thus shows that MDSC cells are not recognized by the T lymphocytes of the (immunologically incompatible) receiver, and suggests that said cells could be used in allotransplantation. This study was not extended to human cells.

Two hypotheses can be proposed to explain the limited self-renewal capacity shown by the different multipotent cells isolated up to now:

firstly, it can be assumed that the various studies were not carried out on true "stem" cells but rather on intermediate precursors. This hypothesis is all the more supported by on the fact that stem cells can readily be confused with precursors in terms of plasticity. Further, contamination of the culture by precursors is facilitated by their abundance compared with "stem" cells, but their lifetime is limited;

secondly, it is also possible to envisage that the "stem" cells could not be maintained in vitro in the undifferentiated state as the culture conditions were unsuitable.

It should also be noted that to date, many of the methods carried out to obtain multipotent cells use bone marrow as the cell source. However, removing cells from the bone marrow is a difficult operation involving risks for the patient and representing a meager source of stem cells. Thus, it is a technique that is poorly suited to the large scale production of stem cells.

Several teams of investigators have therefore attempted to develop methods that allow isolation of multipotent cells from other, more abundant tissues, which methods do not run major risks for the patients. From this standpoint, adipose tissue a priori constitutes a promising source. However, to date, while the presence of multipotent cells has been demonstrated in human adipose tissue, the results have been fairly disappointing. The cell populations obtained are often heterogeneous and cannot be maintained in culture in vitro beyond two or three population doublings. Further, to date, no investigators have reported the production from human adipose tissue of multipotent cells with a negative HLA class I phenotype. This characteristic, which is not required for self-grafting use, becomes indispensable if cells are intended for broader therapeutic use, in particular for allo-transplantation.

For example, International patent applications WO 01/62901 (Artecel Sciences Inc) and EP 1 077 254 (Zen Bio Inc) describe the production, from adipose tissue, of populations of stromal cells with a multipotent character. Said populations are heterogeneous and contain, inter alia, pericytes, endothelial cells and smooth muscle cells (see Erickson et al., Biochem. and Biophys. Res. Com. 290, 763-769, (2002)). Their self-renewal capacity is extremely limited and an analysis of the expression of surface markers confirms that they are positive HLA class I. The characteristics of said cell populations are thus not compatible with their use in therapy.

American patent US 2002/0076400 (Katz et al.) and WO 00/53795 (University of Pittsburgh and the Regents of the University of California) also describe the production of multipotent cell populations from human adipose tissue. Said cell populations can be differentiated into adipocytes, osteoblasts, chondrocytes and myocytes. According to the authors, they can be maintained in culture in vitro for at least 15 cell transfers without losing their multipotent character. No information is given regarding the corresponding population doubling. Before subjecting the cells to successive transfers, a telomerase activity was detected in said population, which was heterogeneous. This activity was not measured after successive transfers. No surface marker analyses were carried out. The expression of HLA class I antigens was thus not determined.

The present invention overcomes the disadvantages of the techniques described above.

The present inventors have developed a method that can reproducibly isolate multipotent "stem" cells from the adipose tissue of young children and multiply them in the undifferentiated state in large quantities in vitro for more than 200 population doublings. Their therapeutic use thus becomes possible. In its major aspect, the invention concerns a method for producing stem cells from adipose tissue and also the use of the stem cells obtained.

In the context of the present invention the following terms signify:

| | |
|---|---|
| Self-renewal: | the capacity of division without altering the initial characteristics of the cell. |
| stem cell: | multipotent cell with a high self renewal capacity, with a telomerase activity and capable of becoming quiescent. |
| adult stem cell: | stem cell other than an embryonic stem cell deriving, for example, from a newborn, a child or an adult. |
| multipotent or multipotential: | capable of differentiating into at least two cell types. |
| quiescent: | the capacity of a cell to remain in a non-proliferating and non-senescent state. |

More particularly, the invention concerns a method for producing human multipotent stem cells from adult tissue in particular from adult adipose tissue. In a first step, the method comprises culturing cells deriving from a tissue sample, preferably adult adipose tissue. Other types of tissue which can be used include the muscle, bone marrow, liver, and nervous system. After 12 hours of culture, the cells are separated into two sub-populations depending on their adhesion rate, a first cell population "CA" adhering in less than 12 h, and a second cell population "CS" adhering more slowly and occurring, after 12 hours of culture, in suspension in the culture medium. The "CA" population is then enriched until a population of cells that is capable of becoming quiescent is obtained. From this stage, intensive proliferation of stem cells of the "CA" population can then be induced.

In a preferred variant of the invention, the method for producing multipotent human stem cells comprises the following steps:

a) enzymatic digestion of a sample of adipose tissue;
b) recovering a cell fraction that is free of adipocytes, containing all of the cell types present in the preparation obtained in (a) with the exception of adipocytes;
c) in vitro culture for at least 12 hours of the cell fraction obtained in step (b),
d) selection of two cell sub-populations termed population "CA" and population "CS", population "CA" having an adhesion rate of less than 12 hours, and population CS having an adhesion rate of more than 12 hours;
e) enriching population "CA" until a population of cells is obtained that are capable of becoming quiescent;
f) optionally, inducing enhanced proliferation of stem cells of the "CA" population, for example by adding a growth factor.

Figure 19:
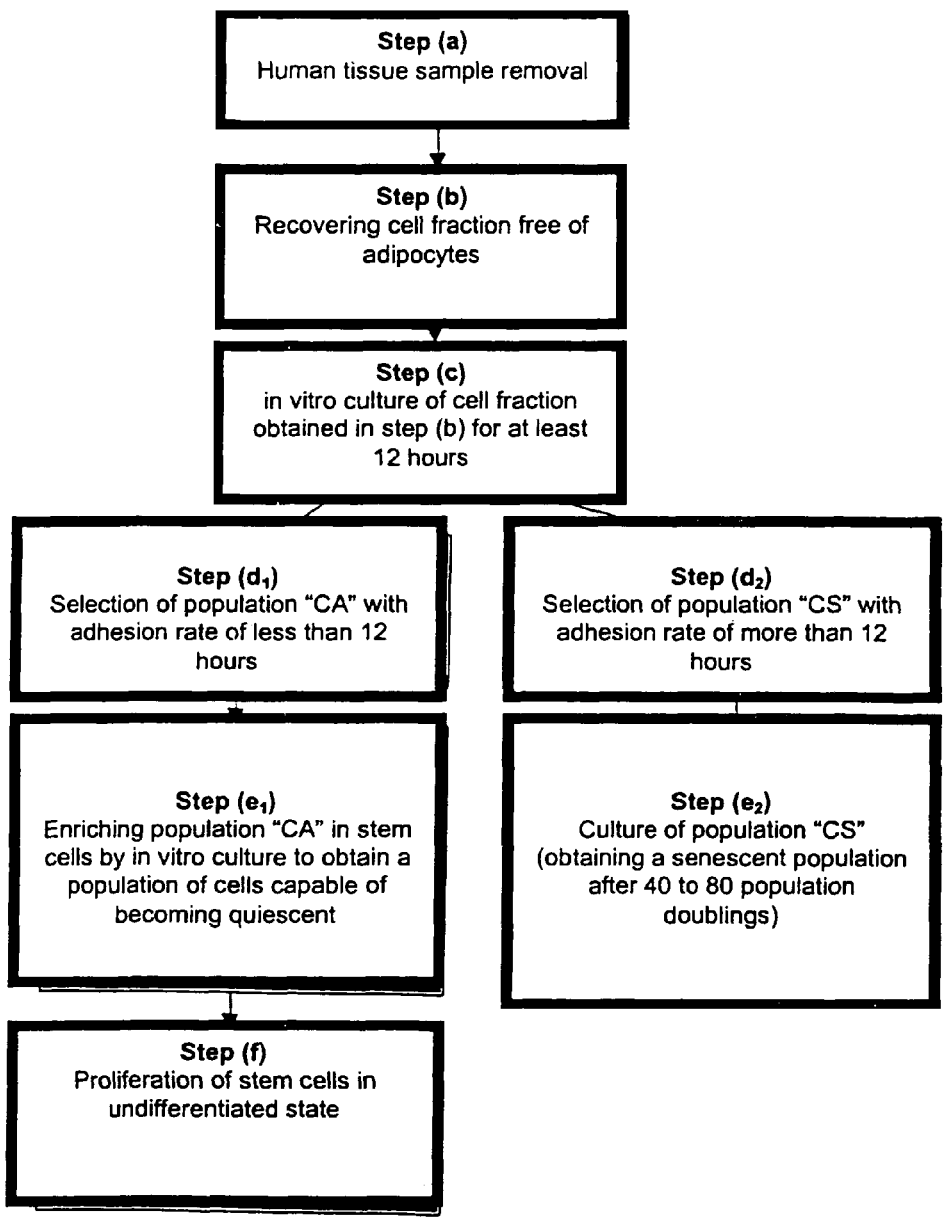

FIG. 19 shows a diagram of a preferred variant of the method of the invention.

Step (a): Enzymatic Digestion of a Sample of Adipose Tissue:

The enzymatic digestion step is preferably carried out by bringing the adipose tissue sample into contact with an enzymatic preparation such as collagenase for a short period, i.e. a maximum of 10 minutes, and more preferably 5 to 10 minutes, or 5 to 8 minutes. This allows complete dissociation of the tissue while avoiding damage to certain cell types and thus results in better viability of all of the cell types.

Regarding the nature of the adipose tissue, it preferably derives from a healthy individual, preferably a healthy young child, preferably below 10 years of age, for example a newborn or a child of 2 to 3 months to 8 years old. The child may be male or female.

The age of the donor appears to be an important point. Indeed, a certain amount of data obtained from hematopoietic "stem" cells strongly suggests that the "stem" cells not only reduce in number with the age of the individual but also undergo an ageing process resulting in a loss of functionality (Geiger H and Van Zant (2002), Nature, vol 3, no 4, 329-333).

If this data is extrapolated, the adipose tissue of young children appears to constitute a more abundant and more functional source of "stem" cells than the adipose tissue of adult individuals.

The adipose tissue sample can derive from any anatomical site, but is preferably a sample of tissue of extramedullary origin, more particularly from the umbilical region or from the pubic region or from the inguinal region or from the perineal region or from the abdominal region or from the subcutaneous region. The pubic, pre-pubic, inguinal and umbilical regions are more particularly preferred.

Step (b): Recovery of a Cell Fraction Free of Adipocytes:

The adipose tissue that has undergone enzymatic digestion is then treated to remove the adipocytes. An adipocyte free cell fraction is then recovered, containing all of the cell types present in the adipose tissue (for example pre adipocytes, stem cells, endothelial cells, pericytes, mastocytes . . . ) with the exception of adipocytes.

The adipocytes can be eliminated by any appropriate means. Centrifuging is particularly effective since all of the cells of interest can be found in the centrifugation pellet while adipocytes float in the supernatant.

It is important to note that this step in the procedure is carried out without filtering, enabling all cell types other than the adipocytes to be preserved in culture. In conventional techniques for preparing cells from adipose tissues, filtration steps, successive or otherwise, are generally carried out, depending on the authors, before or after centrifuging, to eliminate waste. This step, however, risks the loss of certain cell types.

Step (c): In Vitro Culture:

The cell fraction obtained during step (b) is then cultured for at least 12 hours, preferably for 12 to 80 hours, for example 12 to 72 hours.

For this step of the procedure, the cells are seeded at a density in the range 1000 to 5000 cells/cm$^2$, for example 1000 to 3500 cells/cm$^2$. Multipotent cells are not actually present in great numbers compared with other cell types, and high density seeding thus ensures that each dish contains this cell type.

The culture medium used for this step of the method is normally a DMEM type culture medium supplemented with foetal calf serum without the addition of other growth factors. As an example, a particularly suitable medium is: DMEM+ 10% decomplemented foetal calf serum+antibiotics (100 U/ml penicillin, 100 µg/ml streptomycin).

The cell yield for this step varies depending on the sample: 1000 to 5000 cells per mg of tissue.

Step (d): Selecting Two Cell Sub-Populations:

The step of enrichment of multipotent stem cells starts by the separation, at the start of the culture step (c), of two cell sub-populations as a function of their adhesion rate:
   a cell population CA adhering in less than 12 h
   a cell population CS adhering more slowly (48 to 72 h).

After 12 hours of culture, population CS occurs in suspension in the culture medium while population CA adheres to the dishes.

"Stem" cells are found only in sub-population CA while the second sub population contains multipotent precursors which die after about 60 population doublings. While population CS therefore cannot be used for the production of stem cells, it can nevertheless be used for other applications. The CS population has the following characteristics:
   i) it is multipotent,
   ii) it has a negative HLA Classe I phenotype,
   iii) it has a normal caryotype,
   iv) its self-renewal capacity is preserved for about 40 to 60 population doublings,
   v) its proliferation rate is not affected by Leukemia Inhibitory Factor (LIF).

This cell population thus lends itself to therapeutic and cosmetic uses comparable to those normally known for multipotent cells of the prior art.

The step of selection of the rapidly adhering population (population CA) is important as it allows, from the start of culture, a lesser dilution of the "stem" cells with respect to the bulk of the different precursor cells by carrying out an initial selection.

Step (e) Enrichment for Stem Cells:

The CA and CS populations are then cultured in identical conditions. For population CA, this culture produces a substantial enrichment in stem cells. This enrichment step is based on the fact that the precursors have a lifetime that is limited compared with the stem cells (which are immortal, in theory). During the initial population doublings, the precursors will multiply much more rapidly than the stem cells, then they will start to die, by 50 to 80 population doublings. At this stage, the population is highly enriched in stem cells.

During this step, each cell transfer is carried out when the cells reach 80% confluence and high density seeding is carried out, i.e. at a density in the range 1000 to 5000 cells/cm$^2$, preferably in the range 1000 to 3500 cells/cm$^2$, and more particularly in the range 2000 to 2500 cells/cm$^2$.

At each cell transfer, the cells are diluted by a maximum of 2 or 3 for about 50-80 population doublings (stage at which the CA population is highly enriched in "stem" cells and the CS population dies, which corresponds to the death of the precursors). This step is indispensable based on the hypothesis that the true "stem" cell, which is quiescent in its normal state, divides more slowly than the precursor. Greater dilution of the cells during the trypsination steps could run the risk of losing these multipotent cells in certain culture dishes.

After about 50 to 80 population doublings (for example 60 population doublings), the CS population has the characteristics of a senescent population (loss of proliferative potential and loss of multipotentiality) and dies. In contrast, the CA population at the same stage proliferates more slowly compared with the first population doublings (population doubling time about 72 hours compared with an initial mean doubling time of about 36 hours) and is capable of becoming quiescent.

The CA population can be considered to have reached quiescence when it exhibits the following characteristics:
   spontaneous stoppage of proliferation at about 70% confluence;
   confluence may be achieved at this stage in the presence of bFGF or other growth factors. A reduction in the population doubling time from 72 hours to about 36 hours may be observed;
   the effect of bFGF or other growth factors on the doubling time is reversible.

Further, a measurement of the endogenous X-gal activity determined at a pH of 6 in the CA population is negative (less than 0.05%), confirming that this population is in the quiescent state rather than in the senescent state.

The culture medium employed for this enrichment step is typically a medium without added growth factors, for example the culture medium DMEM+10% decomplemented foetal calf serum+antibiotics (100 U/ml of penicillin, 100 µg/ml of streptomycin).

Step (f): Induction of Stem Cell Proliferation in the Undifferentiated State:

After reaching quiescence, proliferation of cells in the CA population is induced by trypsination and dilution of the cells in new dishes. Preferably, the cells are subjected to a trypsin treatment at 80% confluence and are diluted 2 to 10 times, preferably 5 to 10 times in identical new culture dishes.

The addition of a growth factor at this stage, for example basic fibroblast growth factor (bFGF), PDGF, EGF, NGF or SCF allows intensive proliferation of "stem" cells of the CA population. The addition of human bFGF at this stage is particularly preferred.

The addition of growth factors such as bFGF incorporated, for example, at a concentration of about 3 to 20 ng/ml of medium, in particular 5 to 10 ng/ml, not only halves the population doubling time (for example the population doubling time without bFGF is about 72 hours, while it is about 36 hours with bFGF), but also allows the population to reach confluence. Without growth factors, proliferation of a quiescent population of stem cells of the invention can be provoked by trypsination and dilution, but proliferation will spontaneously stop at about 70% confluence. Since confluence is indispensable in vitro for initiating the differentiation of many cell types, the use of growth factors such as bFGF must be envisaged for in vitro production of this type of differentiated cell.

This step of the method is clearly distinguished from prior art methods. In the method of the invention, growth factors such as bFGF are only used after obtaining a population that can become quiescent. In contrast, bFGF is generally used from the start of culture of freshly isolated cells ((Tsutsumi S et al., Biochemical and Biophsysical Research Communications 288, 413-419 (2001)). This very early use of bFGF has a peverse effect as it stimulates not only proliferation of true "stem" cells but also of all precursors. This has the result of further increasing the precursor/stem cell ratio, resulting in a loss of this rare cell type by dilution. According to the invention, an innovating point is the use of bFGF when the mass of precursors has disappeared and the population, highly enriched in "stem" cells, becomes quiescent.

Inducing proliferation of stem cells can produce large quantities of these multipotent cells. The cells produced can be recovered from the culture media using conventional methods.

In summary, the method of the invention comprises a number of innovating elements that can optimize the production of stem cells:
   rapid digestion with an enzymatic preparation such as collagenase (step a)) which allows complete dissociation of the tissue while preventing damage to certain cell types;
   the absence of filtering steps in step b), to avoid loss of certain cell types on the filters;
   high density cell seeding during culture steps d) and e). Indeed, multipotent cells are in small supply compared with other cell types;
   isolation of 2 sub populations "CA" and "CS", as a function of their adhesion rate;
   late use of a growth factor such as bFGF after the cells have become quiescent (step f).

In carrying out the method of the invention, the present inventors have established a plurality of human multipotent lines from the adipose tissue of young children. The technique of the invention has been validated for a several adipose tissue samples, for example those shown in Table 1 (see the Examples below).

The cells of the invention have many characteristics of stem cells, for example: the capacity to become quiescent; quiescence stops if induced to do so with bFGF or other growth factors, resulting in an intense resumption of proliferation (reversible effect of said growth factors secreted in vivo into the organism during damage to the body); maintenance of multipotentiality over a large number of population doublings; significant telomerase activity; normal karyotype.

More particularly, the cells of the invention are multipotent adult human stem cells, characterized in that they have:
   i) a capacity for self-renewal that is retained over at least 80 population doublings, and preferably over at least 100 population doublings;
   ii) significant telomerase activity
   iii) a negative HLA class I phenotype;
   iv) a normal karyotype;
   v) a capacity to become quiescent.

The self-renewal capacity of the cells of the invention is preserved over at least 80 population doublings, preferably at least 100 or 130 population doublings, and more particularly over at least 200 population doublings. This means that the cells of the invention are capable of undergoing at least 80 or 130 or 200 population doublings without losing their original characteristics. In other words, the multipotentiality, telomerase activity, negative HLA class I phenotype, normal karyotype and the capacity to become quiescent are retained throughout all of these population doublings.

The telomerase activity of the cells of the invention, which can be measured by conventional techniques, is particularly important. In accordance with the definition of a "stem" cell by Watt and Hogan (Science, vol 287, February 2000), telomerase activity normally means that the cells obtained should be capable of infinite self-renewal. Telomerase activity is only present in embryonic cells and, in the adult, in tumour cells and "stem" cells. This activity thus confirms that the cells are stem cells.

The level of the endogenous telomerase activity of the cells of the invention preferably corresponds to at least 20%, for example 20% to 50% of the telomerase activity of a reference cell line, more particularly 22% to 50%. The reference line is typically a transformed line having endogenous telomerase activity, such as the transformed human line HEK293T (Human Embryonic Kidney 293 immortalised with T antigen). This activity can be measured at any stage. It is preferably measured after 30 or 40 population doublings, for example at the quiescent stage after about 60 population doublings.

Regarding the immunological characteristics of the cells of the invention, they differ from a conventional somatic cell. These cells do not express molecules of the HLA class I system on their surface (confirmed by flow cytometry), nor do they express HLA class II on the surface. The molecules of the HLA class I system present self and non self peptides to CD8+cytotoxic T lymphocytes, hence their critical role in graft rejection reactions. The absence of surface HLA class I molecules suggests the "universal" nature of the stem cells of the invention in transplantation. Said cells could be used for allo-transplantation with no risks of rejection by the host, independently of its genotype.

The negative HLA class I and/or class II phenotype can be analysed by any conventional technique. It is preferably measured after 30 or 40 population doublings, for example at the quiescent stage at about 60 population doublings, or at a later stage, i.e., after quiescence, for example at 100 or 120 population doublings. During the first population doublings, surface expression of HLA class I molecules is low but significant, then disappears at later stages (for example after quiescence between 50 and 80 population doublings) corresponding to the stage at which early precursors disappear.

In the context of the invention, the expression "HLA negative" means that the stem cells of the invention have a level of surface expression of HLA class I molecules that cannot be detected by flow cytometry with single labeling (using a fluorochrome). Preferably, the "HLA negative" cells of the invention also have a level of surface expression of HLA class II molecules that cannot be detected by flow cytometry with single labeling.

Further, thanks to a phenomenon of immunoprivileged behavior, the cells of the invention in the differentiated state most probably do not induce a rejection reaction in a host, independently of its genotype.

The cells of the invention have a normal karyotype, confirming that they are not transformed.

In the normal state, the cells of the invention are quiescent (Blau H M et al, Cell, 105, 829-841, Jun. 29, (2001)) and start proliferating again in the presence of bFGF. Quiescence is a particular characteristic of stem cells. Beyond a certain number of population doublings, "non-stem" cells become senescent. The quiescent state can, in theory, be maintained indefinitely. For the cells of the invention, the inventors have maintained this state for periods of up to one year. Proliferation can then be induced by trypsination and dilution, optionally accompanied by adding a growth factor. At quiescence, the cells of the invention stop proliferating spontaneously before reaching confluence, for example between 50% and 90% of confluence, more particularly between 60% and 70% of confluence.

One important characteristic of the cells of the invention is their multipotentiality. They are capable of differentiating into at least two cell types. More particularly, they are capable of differentiating into cells of endodermal origin (for example the liver) or ectodermal origin (nerve cells: astrocytes, oligodendrocytes and neurones) or of mesodermal origin. Examples of cells of the mesodermal lineage that can be cited are adipocytes, osteoblasts, myocytes, endothelial cells and chondrocytes.

It has been demonstrated that the cells of the invention, even at late stages, are capable of differentiating into functional adipocytes (demonstrated by lipolysis, GPDH activity, adipocyte markers), into functional osteoblasts (demonstrated by the presence of osteoblast markers and calcification of the extracellular matrix), into functional myocytes and into endothelial cells. This differentiation can take place in vitro or in vivo.

It has been demonstrated that CA cells of the invention have, at the single cell level, the capacity of differentiating into adipocytes, osteoblasts, myocytes and into endothelial cells, i.e. each CA cell of the invention is capable of differentiating into these four cell types. In contrast to adipocytes, osteoblasts and myocyte cells which belong to the "Limb bud mesoderm", endothelial cells derive from the visceral mesoderm. The cells of the invention are thus not limited to differentiation into cells of the mesenchymal lineage but can more generally differentiate into cells of the mesodermal lineage.

The inventors have investigated the presence of markers on the stem cells of the invention. They have established that they express the transcription factors Oct-4 and Rex-1, and the surface antigen ABCG2 (ABC transporter responsible for the SP phenotype, Zhou S et al., Nature Medicine, 7, no 9, September 2001, 1028-1034). The Oct-4 and Rex-1 transcription factors are expressed specifically in embryonic stem cells of mice and humans. Oct-4 is indispensable to maintaining the pluripotentiality of mouse embryonic stem cells. It has also been shown that Oct-4 is expressed by human embryonic stem cells.

It has also been observed that the stem cells of the invention do not react to Leukemia Inhibitory Factor (LIF), at concentrations of about 10 ng/ml. LIF produces no changes in morphology or proliferation of the cells. In accordance with results obtained by other investigators with human stem cells, in particular embryonic stem cells, it can therefore be concluded that the cells of the invention most probably do not express the receptor for LIF (LIF-R) and are thus LIF-R negative.

Preferably, the cells of the invention, after having reached quiescence, stably exhibit the following phenotype in vitro:
  HLA class I negative,
  HLA class II negative,
  CD3 negative,
  CD13 positive,
  Oct-4 positive,
  Rex-1 positive,
  ABCG2 positive.

These phenotype characteristics are associated with a normal caryotype and significant telomerase activity. Preferably, the cells are also LIF-R negative. This phenotype is stably conserved in vitro, i.e. in the absence or presence of FGF-2 and at concentrations of foetal calf serum that may exceed 10%. The phenotype is also preserved at high seeding densities, and beyond 140 population doublings.

The doubling time for the cell populations of the invention varies as a function of the proportion of stem cells present. As an example, before reaching quiescence, the doubling time is about 36 to 40 hours, reflecting the presence of precursors in the CA population. As the stem cell proportion increases, the doubling time also increases, and reaches about 70 to 80 hours at quiescence. Stem cells divide much more slowly than precursors. After quiescence, adding growth factors such as bFGF can significantly reduce the doubling time, for example to about 36 hours, allowing intensive and rapid production of stem cells.

The cells of the invention can be genetically modified then selected to introduce or cause expression of a novel characteristic, for example by ablation or modification of an endogenous gene or for expression of a transgene such as a reporter gene or a gene the expression product of which has therapeutic properties, under the control of a suitable promoter, for example ubiquitous or tissue-specific promoter.

The expression of a transgene or DNA or RNA can be either constitutive or reversibly or irreversibly inducible. The heterologous DNA or RNA of interest can be carried by any expression vector, for example a viral vector (including retroviral vectors), inert vectors, plasmid vectors or an episomal vector.

The vectors can be introduced into the cells by transfection, for example using chemical agents such as calcium phosphate, by lipofection or by using a physical agent such as electroporation, micro-injection, etc. . . . Said vector can be maintained in the cell either in the epsiomal form or integrated into the genome, randomly or in a targeted manner.

Said genetically modified cells can be used in gene therapy to supply an expression product of a heterologous gene to an individual. Thanks to the multipotent nature and HLA class I negative nature, the stem cells of the invention are particularly suitable for this type of application.

When the cells of the invention are transduced or transfected by a reporter gene, they can be used to carry out a number of studies. As an example, the plasticity of multipotent adipose tissue stem cells can be investigated using stem cells transfected with the lacZ gene coding for β-galactosidase (blue after staining with Xgal). These labeled cells can be used for in vitro and in vivo experiments.

For example, in vitro, the plasticity of said cells can be studied by co-culture experiments. In particular, the capacity of said cells (of mesodermal origin) to differentiate into cells of endodermal origin (for example the liver) and into cells of ectodermal origin (nerve cells: astrocytes, oligodendrocytes and neurons) can be studied.

In vivo, the labeled cells can also be transplanted into the athymic (nude) mouse which has a deficient immune system and which thus cannot reject these cells. The transplanted cells do not produce a tumor. The regenerating power of said cells is only visible if suitable lesions are initially produced in the mouse to be transplanted.

The stem cells of the invention do not express surface HLA class I molecules, in contrast to the majority of somatic cells. The absence of said proteins the immune function of which is crucial, suggests that said stem cells can be transplanted universally without any rejection reaction.

Indeed, the inventors have demonstrated that the cells of the invention can be transplanted into immunocompetent mice without a rejection reaction 6 months after transplantation.

The CA cells of the invention are thus characterized in that in vivo they have an immunoprivileged behavior, i.e. they do not give rise to a rejection reaction when they are transplanted into an immunocompetent mammal (such as a mouse), even after more than 10 days following transplantation, preferably after 80 days, and more preferably after 6 months. Transplantation can be allogenic or xenogenic. The absence of a rejection reaction can be determined using techniques that can demonstrate the absence of lymphocyte infiltration, for example using anti-CD3 antibodies or using a hematoxylin stain.

Surprisingly, it has also been shown that in vivo, the cells of the invention have the capacity to migrate in the undifferentiated state. 50 days after transplantation of CA cells of the invention into the Anterior Tibialis of an immunocompetent mouse, the presence of said cells was observed in the damaged tissue adjacent to the injection site. This behavior suggests that the cells of the invention can contribute, by recruitment, to restoration of a normal phenotype at anatomical sites other than the injection site.

The invention also concerns enriched populations of multipotent cells, characterized in that they comprise the stem cells of the invention, and in that they are free of adipocytes, fibroblasts, pre-adipocytes, endothelial cells, pericytes, mastocytes and smooth muscle cells.

The populations of the invention are preferably entirely homogeneous, i.e. they contain only stem cells. More particularly, the populations are clonal populations.

The invention also concerns the production of differentiated cells from the stem cells of the invention.

For example, the invention concerns the production of differentiated cells of the mesodermal lineage, characterized in that stem cells of the invention are cultivated from confluence, in the presence of a suitable differentiation medium.

The following medium can be cited as a medium that allows adipocyte differentiation:
DMEM medium/Ham's F12 (vol/vol, 1:1), supplemented with antibiotics, for example 100 U/ml of penicillin, 100 μg/ml of streptomycin,
5 μg/ml human insulin (Sigma),
10 μg/ml of human transferrin (Sigma),
PPARγ activator, for example 1 μM of BRL49653, or 2 μm of Ciglitazone (Biomol),
100 to 250 μM of isobutyl-methylxanthine (IBMX)
1 μM of dexamethasone
0.2 nM of triiodothyronin (T3 Sigma).
48 to 72 hours later, this medium is replaced by the same medium containing no IBMX or dexamethasone.

The following medium can be cited as a medium that allows osteoblast differentiation:
DMEM supplemented with antibiotics, for example 100 U/ml of penicillin, 100 μg/ml of streptomycin,
10% of decomplemented foetal calf serum,
0.1 μM of dexamethasone (SIGMA),
10 mM of β-glycerophosphate (SIGMA)
50 μg/ml of ascorbic acid (SIGMA).
The medium is replaced every 2-3 days over a period of between 15 and 20 days.

The following medium can be cited as a medium that allows myocyte differentiation:
The medium sold under the trade name PromoCell, or DMEM medium
2% of decomplemented foetal calf serum
antibiotics (for example 100 U/ml of penicillin, 100 μg/ml of streptomycin)
The medium is replaced every 2-3 days over 4 to 6 weeks.

The following medium can be cited as a medium that allows differentiation into endothelial cells:
DMEM medium supplemented with antibiotics,
10 ng/ml of human $VEGF_{121}$ (SIGMA).

For adipocyte, osteoblast and myocyte differentiation, the stem cells are normally seeded at a density of about 10 000 to 25 000 cells/cm$^2$.

Prior to the differentiation step, the cells are normally seeded at a density of 25000 cells/cm$^2$ in a proliferation medium (DMEM supplemented with 10% FCS and 2.5 ng/ml of FGF-2). Two days later, the culture medium is changed in the absence of FGF-2 for 48 hours. The cells are then maintained in a differentiation medium for 10 days.

The stem cells of the invention are particularly suitable for use in therapy or in cosmetology.

The therapeutic use of the stem cells of the invention include, inter alia, use in transplantation and in gene therapy.

For example, for use in transplantation, the cells of the invention are multiplied in the undifferentiated state in vitro followed by introducing the cells into an individual. The cells can either be injected into the circulation or implanted into an anatomical site. The cells then differentiate in vivo as a function of the damaged anatomical site. As an example, intramuscular transplantation of the stem cells of the invention into an individual with muscle lesions will give rise to muscle differentiation and regeneration. Similarly, the regeneration of adipose tissue can be envisaged by in vivo differentiation of cells to adipocytes.

Transplantation of the cells of the invention can thus be used to regenerate tissue in vivo, for example bone tissue, adipose tissue or muscle tissue.

If necessary, transplantation can be accompanied by implantation of a matrix that can improve tissue regeneration, for example by supplying a physical support for the proliferation of cells or by supplying substances such as growth factors, etc. The matrix may be biodegradable.

In accordance with the invention, transplantation may be autologous or allogenic. The cells of the invention are particularly suited to allo-transplantations because of their HLA class I negative nature. The cells can thus be used in any individual independently of genotype without risking rejection.

In a further variant, the stem cells of the invention can be used in the differentiated state, for example as adipocytes, chondrocytes, osteoblasts, myocytes etc. In this variant, the stem cells are subjected to differentiation in vitro followed by introduction of the differentiated cells into the individual.

For the therapeutic applications of the invention, the stem cells may or may not be genetically modified. When the cells are genetically modified, they can be used in gene therapy to supply an expression product to a patient, for example a heterologous protein. The modified cells can be cultivated in vitro in the undifferentiated state then introduced into the recipient. Alternatively, the cells can be multiplied in vitro in the differentiated state and then introduced to the recipient.

The invention also concerns the implementation of surgical and therapeutic methods using the stem cells of the invention. It also concerns pharmaceutical compositions comprising the stem cells of the invention in association with a physiologically acceptable excipient.

The stem cells of the invention can also be used for in vitro production of proteins, which may or may not be recombinant, particularly therapeutic proteins. In fact, the cells of the invention can be cultivated in vitro for at least 100, for example at least 200 population doublings, and thus constitute an almost inexhaustible source of expression products. The proteins in question can be expression products of genes endogenous to the stem cells, or alternatively, can be expression products of heterologous genes.

The cells of the invention can also be used in screening systems for the identification of active agents, for example gene products, seric extracts, conditioned media, products of animal or plant origin, libraries of pharmacological agents, etc.

For example, the invention comprises a screening method for identifying agents that can modulate the differentiation of cells into cells of a mesodermal line, characterized by:
a) culturing stem cells in accordance with the invention under conditions allowing their differentiation into cells of the mesodermal lineage (for example adipocytes, osteoblasts or myocytes) in the presence of a candidate agent,
b) comparing the differentiation of cells in the presence of the candidate agent with differentiation in the absence of the candidate agent.

The test agent may be an agent that can enhance differentiation or an agent that can prevent or slow or reduce differentiation (anti-differentiation substance) or a substance that can modify the differentiation route.

The invention also comprises a screening method that can identify agents that may have a lipolytic activity, characterized by:
a) culturing stem cells of the invention under conditions allowing them to differentiate into adipocytes;
b) bringing the adipocytes thus obtained into contact with a candidate agent and determining the lipolytic activity of the candidate agent.

The invention also comprises a screening method that can identify agents that may have an anti-lipolytic activity, characterized by:
a) culturing stem cells of the invention under conditions allowing them to differentiate into adipocytes;
b) bringing the adipocytes thus obtained into contact with a candidate agent in the presence of a lipolytic agent;
c) determining the anti-lipolytic activity of the candidate agent.

The invention also comprises a screening method that can identify agents that may have an insulin-sensitising activity, characterized by:
a) culturing stem cells of the invention under conditions allowing them to differentiate into adipocytes;
b) bringing the adipocyte thus obtained into contact with a candidate agent;
c) determining the insulin-sensitising activity of the candidate agent compared with untreated adipocytes.

The invention also pertains to the use of stem cells in cosmetology.

In so far as the stem cells of the invention can differentiate into adipocytes, they can be used in esthetic surgery or repair surgery, for example to reduce the wrinkled appearance of the skin, to reduce scars or various skin blemishes, or to carry out tissue repair. The invention therefore concerns the implementation of said surgical methods using the cells of the invention.

The cells can also be included in cosmetic compositions comprising excipients, vehicles, solvents, colorants, fragrances, antibiotics or other products and additives that are normally used in cosmetic products. The inclusion of the cells in creams, pomades, ointments, gels, various fluids, etc, allows them to be applied directly to the skin or other tissues or phanera. Thus, the invention also pertains to cosmetic compositions containing stem cells of the invention in an undifferentiated state, or containing differentiated cells derived from the stem cells.

KEY TO FIGURES

Different aspects of the invention are shown in the Figures:
FIG. 1: Endogenous β-galactosidase activity of CA and CS cells detected at pH 6.

Xgal staining, which reveals endogenous β-galactosidase activity (signifying cell senescence) carried out at the 60 population doubling stage, corresponding to cell transfer 20 ("T20"), reveals that the CS population is senescent (degree of senescence 0.415±0.025%), while the CA population is simply quiescent (degree of senescence 0.045±0.01%).

Figure 2:
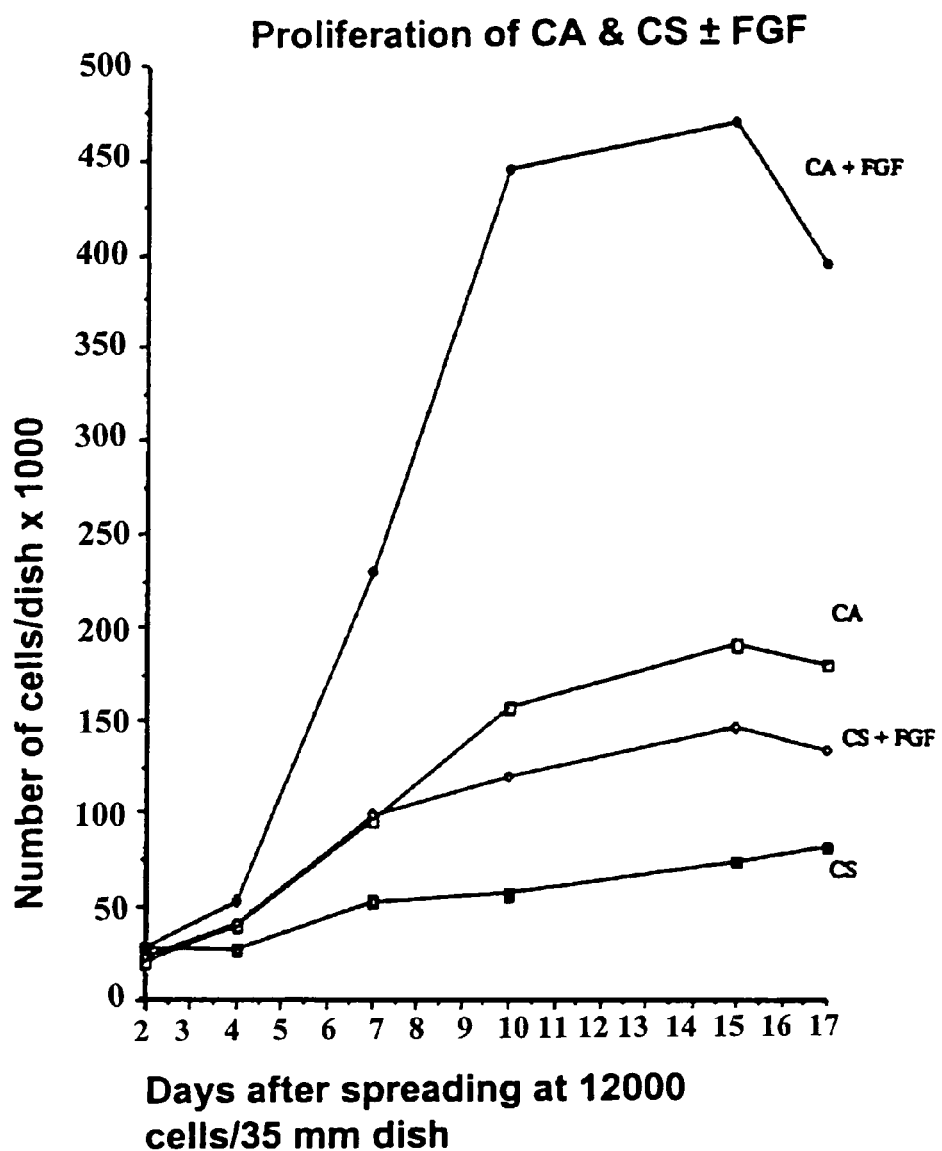

FIG. 2: Effect of bFGF (basic Fibroblast Growth Factor) at a concentration of 5 ng/ml of medium) on CA and CS populations at late stages, i.e. after 50 population doublings.

FIG. 2 shows the proliferation of CA±bFGF and CS±bFGF (Abscissa: days after plating at 12 000 cells/35 mm diameter dish; Ordinate: number of cells (×1000)/dish). Only cells of the CA population effectively respond to bFGF. After 50 population doublings, bFGF has no significant effect on the CS population. These observations confirm the quiescent state of the CA population and the state of senescence in the CS population.

Figure 3:
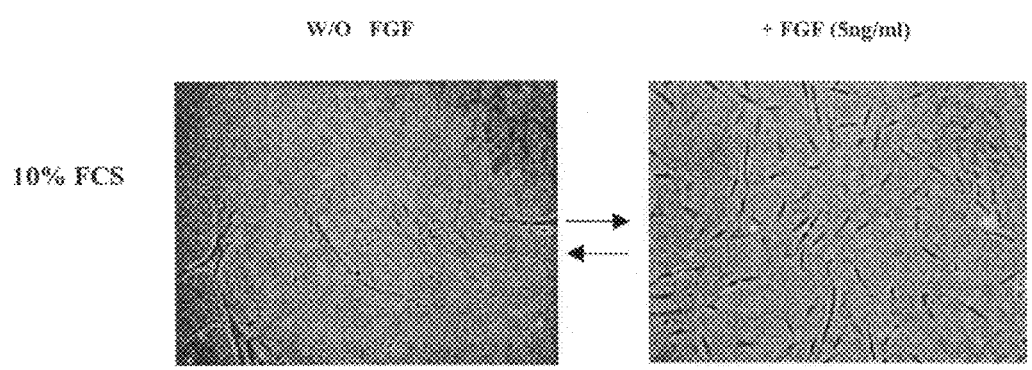

FIG. 3: Morphology of CA cells at late stages (after 50 population doublings) in the absence of bFGF and in the presence of bFGF.
"W/O FGF"=without bFGF
"+FGF"=with bFGF (5 ng/ml)
"FCS"=foetal calf serum bFGF causes a change in cell morphology. When quiescent, the cells are flat and enlarged. In the presence of bFGF, and thus in the proliferative phase, they take on a fibroblast form.

The effect of bFGF is reversible.

Figure 4:
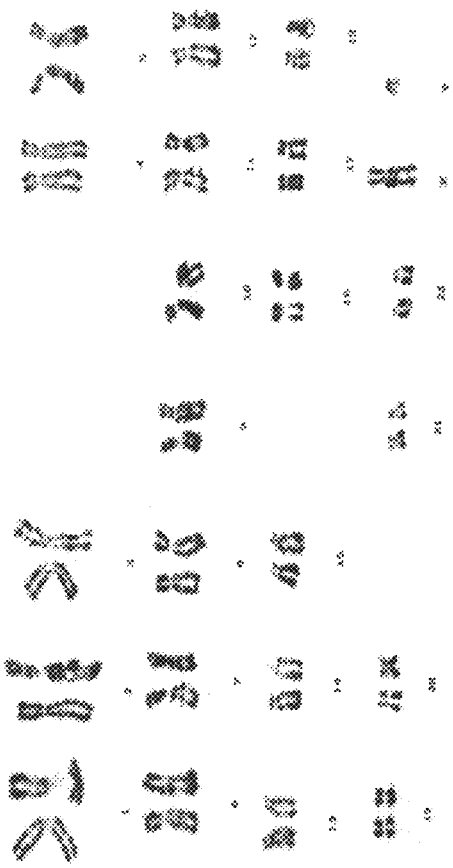

FIG. 4: Karyotype of Primo 2CA cells.

Primo 2 cells were karyotyped for the 2 sub populations CA and CS, with or without bFGF and at different passages. For Primo 2CA cells, the caryotypes were produced at the following stages: T21=80 population doublings; T23=90 population doublings; T34=130 population doublings. In all cases, the karyotypes were normal. FIG. 4 shows an example of a karyotype for Primo 2CA cells.

Figure 5:
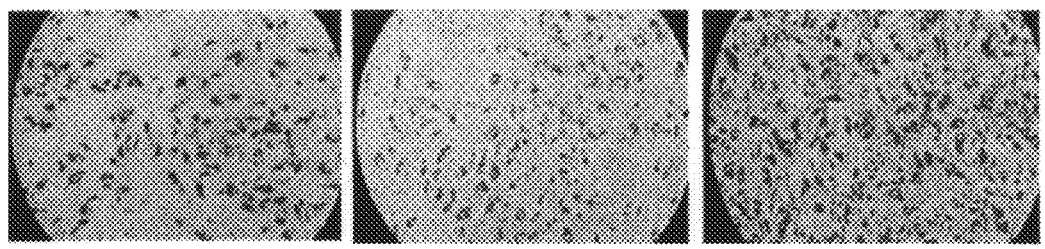

FIG. 5: In vitro differentiation of cells of Primo 2CA and of Primo 2CS into adipocytes at early stages:
CST1: population CS at passage 1 (corresponding to 3 population doublings);
CST7: population CS at passage 7 (corresponding to 21 population doublings);
CAT5: population CA at passage 5 (corresponding to 15 population doublings).
Oil Red O stain.

Figure 6:
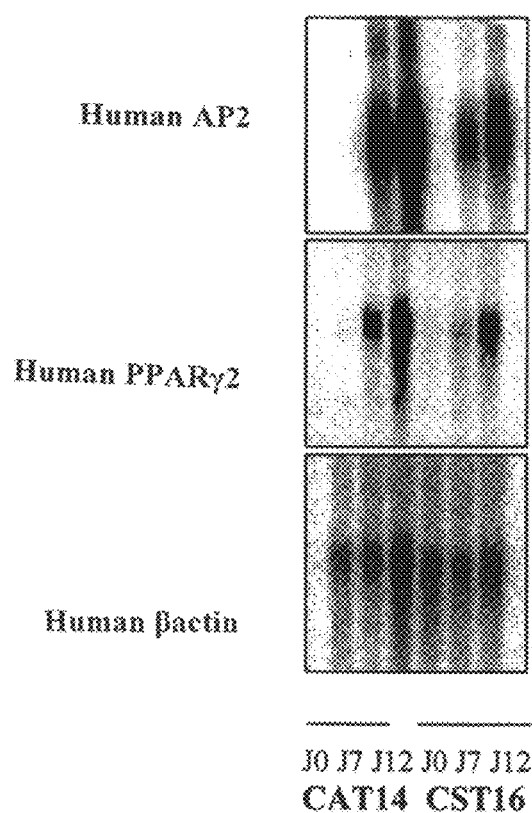
Figure 7:

FIG. 6: Transcriptional expression of adipogenic markers during Primo 2 cell differentiation. Northern Blot analysis.
J0, J7, J12=0, 7 and 12 days, respectively, after induction of differentiation,
CA T14: Primo 2 CA population at passage 14 (corresponding to 42 population doublings).
CS T16: Primo 2 CS population at passage 16 (corresponding to 48 population doublings);

FIG. 7: In vitro differentiation into osteoblasts of CA and CS cells at early passage:
CST1: CS population at passage 1 (corresponding to 3 population doublings);

CST7: CS population at passage 7 (corresponding to 21 population doublings);

CAT5: CA population at passage 5 (corresponding to 15 population doublings).

Alizarin Red stain.

Figure 8B:
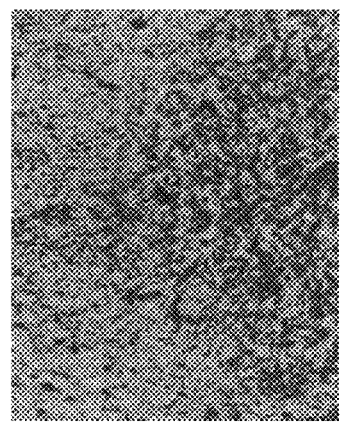
Figure 8A:
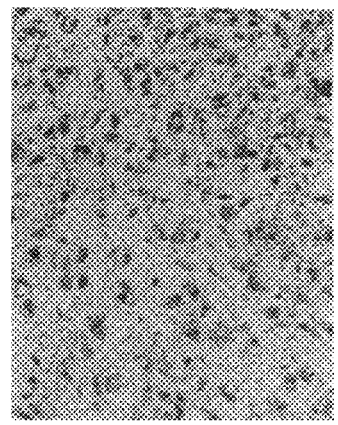

FIG. 8: Differentiation capacity of CA cells at late passage.

A: adipocyte differentiation of Primo 2CA cells. Induction of Adipocyte differentiation was carried out when the cells were at the T30 stage (about 130 population doublings). Oil Red O stain.

B: osteoblast differentiation of Primo 2CA cells. Induction of Osteoblast differentiation was carried out when the cells were at the T30 stage (about 130 population doublings). Alizarin Red stain.

Figure 9:
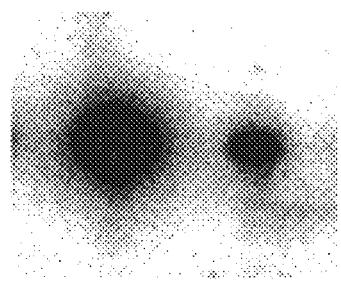
Figure 9:
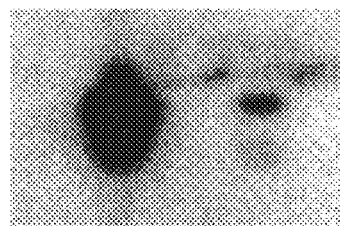
Figure 9:
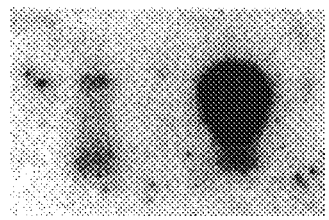

FIG. 9: Functionality of adipocytes and osteoblasts: transcriptional expression of specific markers either for adipocyte differentiation or for osteoblast differentiation.

Transcriptional expression of the markers hPPARγ-2, haP2 and hOC were determined using RT-PCR. The cells used were i) adipocytes (left hand side of Figure), from Primo2CA, adipocyte induction having taken place at stage T32 (about 140 population doublings), and ii) osteoblasts (right hand side of Figure), from Primo2CA, osteoblast induction having taken place at stage T32 (about 140 population doublings).

| hPPARγ-2: | human peroxisome proliferator activated receptor γ: adipocyte marker. |
|---|---|
| haP2: | human fatty acid binding protein: adipocyte marker, |
| hOC: | human osteocalcin (osteoblast marker) |

Figure 10:
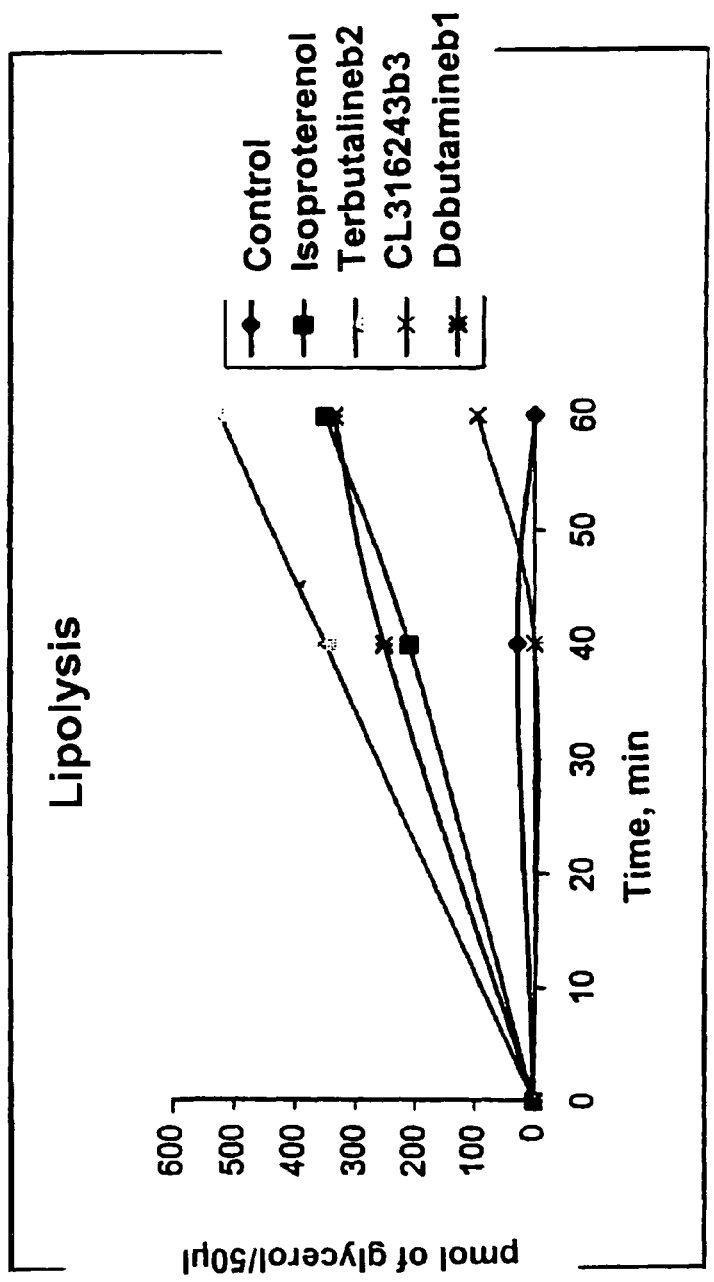

FIG. 10: Functionality of adipocytes: lipolysis capacity of Primo 2CA cells.

Lipolyses were carried out on adipocytes obtained from Primo 2CA T32 cells (about 140 population doublings), with agonists specific for different β-adrenergic receptors. FIG. 10 shows the lipolysis rates obtained and confirms the absence of β3 adrenergic receptors.

Figure 11:
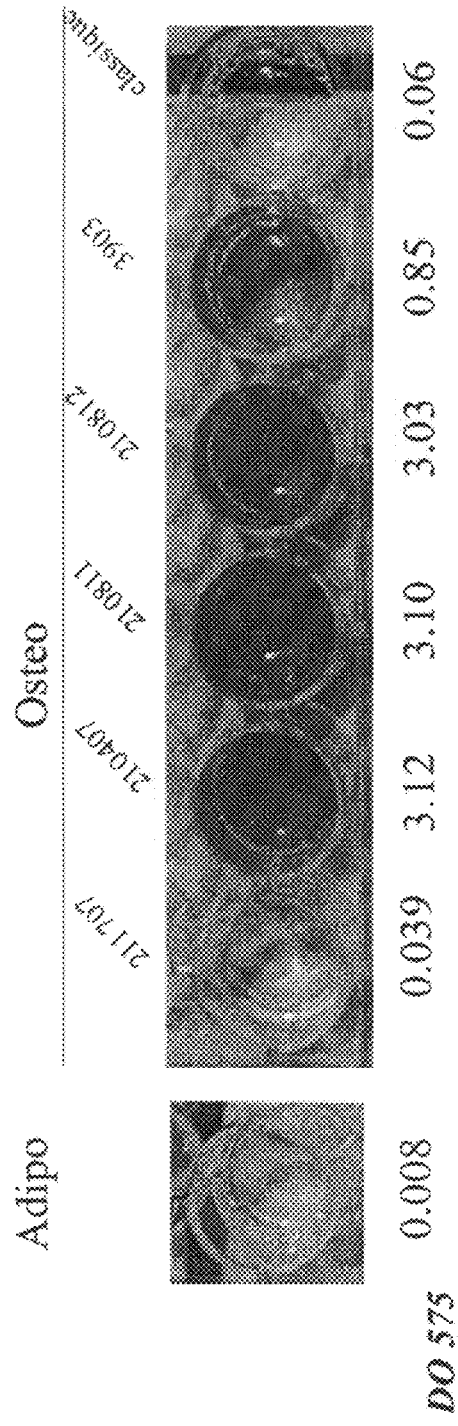
Figure 12B:
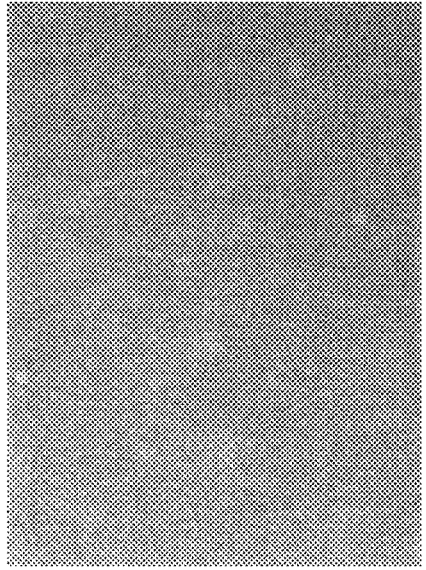
Figure 12D:
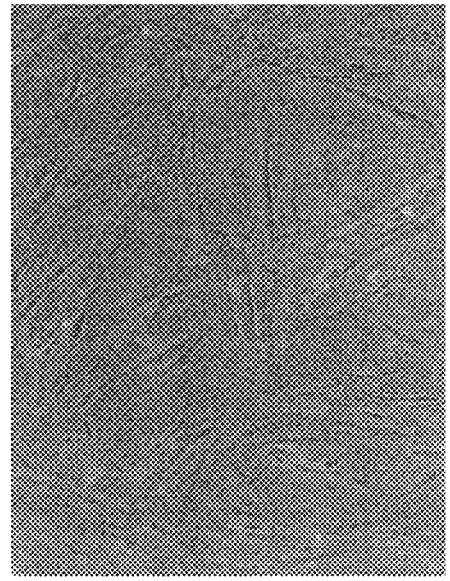
Figure 12A:
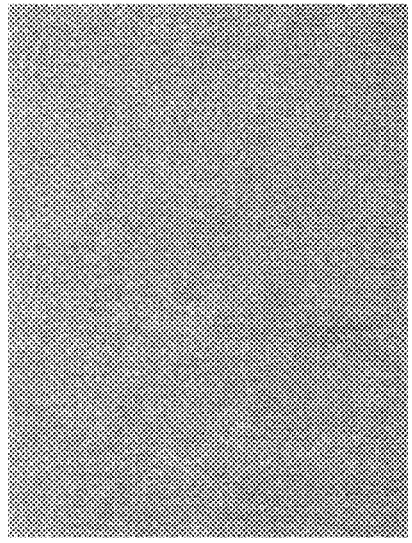
Figure 12C:
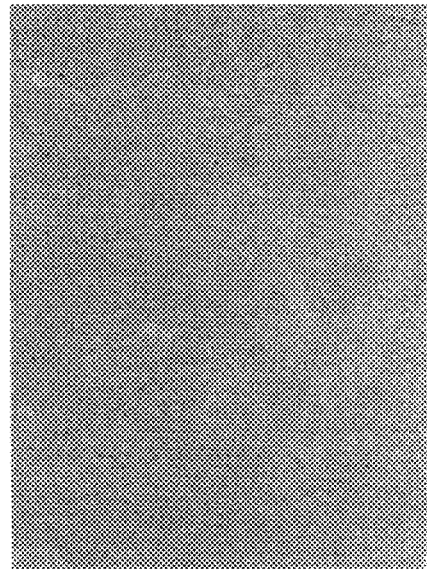

FIG. 11: functionality of osteoblasts: detection of calcium associated with the extracellular matrix.

The extracellular matrix present in culture dishes after lysis of the cell mat was dried then incubated with the solution from a "SIGMA calcium detection kit". The quantity of calcium secreted by the osteoblasts was quantifed by reading the solution using a spectrophotometer (OD 575). Osteoblast functionality was confirmed.

The quantity of calcium secreted by the osteoblasts varied as a function of the serum batch (211707, 210407, 210811, 210812, 3903, conventional). These batches may contain non characterized cytokines, hormones or growth factors present in varying proportions.

The adipocytes did not secrete significant quantities of calcium.

FIG. 12: Morphology of Primo2CA cells as a function of the number of population doublings A: 40 population doublings
B: 100 population doublings: quiescent
C: 150 population doublings: quiescent
D: 150 population doublings+bFGF: proliferative phase.

bFGF causes a change in the morphology of the cells. When quiescent, they are flattened and enlarged. In the presence of bFGF, and thus in the proliferative phase, they take on the form of fibroblasts (see also FIG. 3).

Figure 13C:
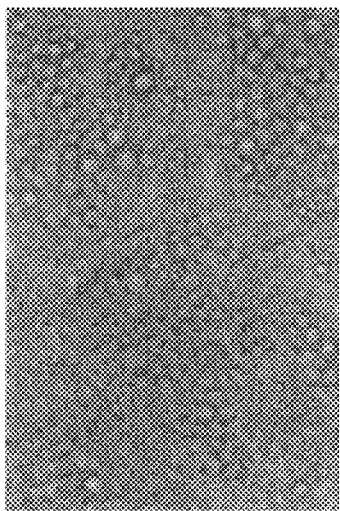
Figure 13B:
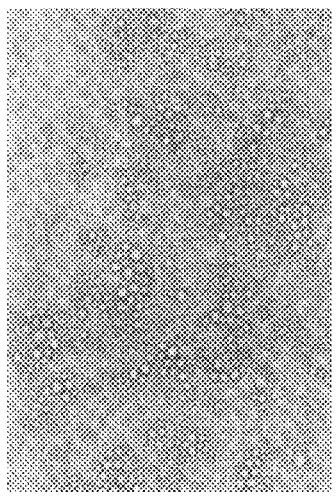
Figure 13A:
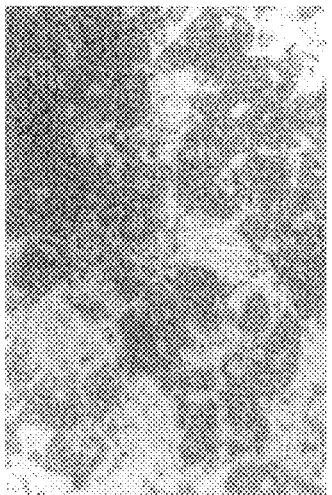

FIG. 13: adipocyte differentiation capacity of Primo 1CA, Primo 3CA and Primo 6CA: Adipocytes after 8 days of differentiation.

A: Primo 1: differentiation induced at 50 population doublings
B: Primo 3: differentiation induced at 40 population doublings
C: Primo 6: differentiation induced at 40 population doublings FIG. 14: Adipocyte differentiation capacity of Primo 1CA, Primo 3CA and Primo 6CA: Oil red O stain A: Primo 1: differentiation induced at 40 population doublings
B: Primo 3: differentiation induced at 25 population doublings
C: Primo 6: differentiation induced at 25 population doublings FIG. 15: Cell marking and flow cytometry analysis.

Demonstration of HLA Class I negative nature of Primo 2CA stem cells.

| Single label: FITC | |
|---|---|
| 1. HELA: | Human tumor cells. HLA Class I positive. |
| 2. SVF: | Adult adipose tissue, no population doublings. HLA Class I positive |
| 3. Primo 2CA: | 120 population doublingss |
| 4. Primo 2CS: | 45 population doublingss |
| Black line: | Mouse IgG: negative antibody control |
| Gray line: | Anti-HLA Class I W6/32 antibodies |

Figure 16:
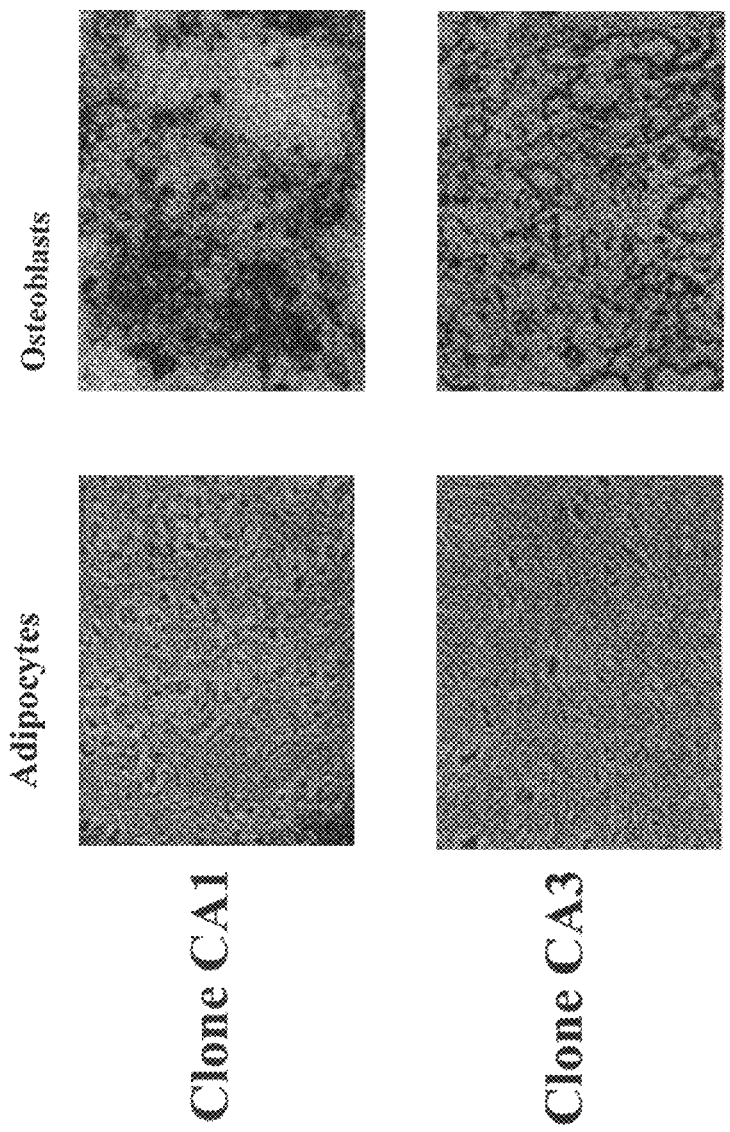

FIG. 16: Obtaining multipotent clones from CA cells.

Clones CA1 and CA3 were placed in a culture medium permitting differentiation into adipocytes and osteoblasts. The adipocytes were revealed by staining with red oil and the osteoblasts were revealed with Alizarin red.

Figure 17:

FIG. 17: Expression of a transgene in CA stem cells.

CA stem cells were transduced by a retrovirus expressing a gene for resistance to an antibiotic, puromycin, and the reporter gene LacZ. They were then selected in the presence of puromycin. The selected cells all expressed the LacZ gene, revealed in situ by β-galactosidase activity.

Figure 18:
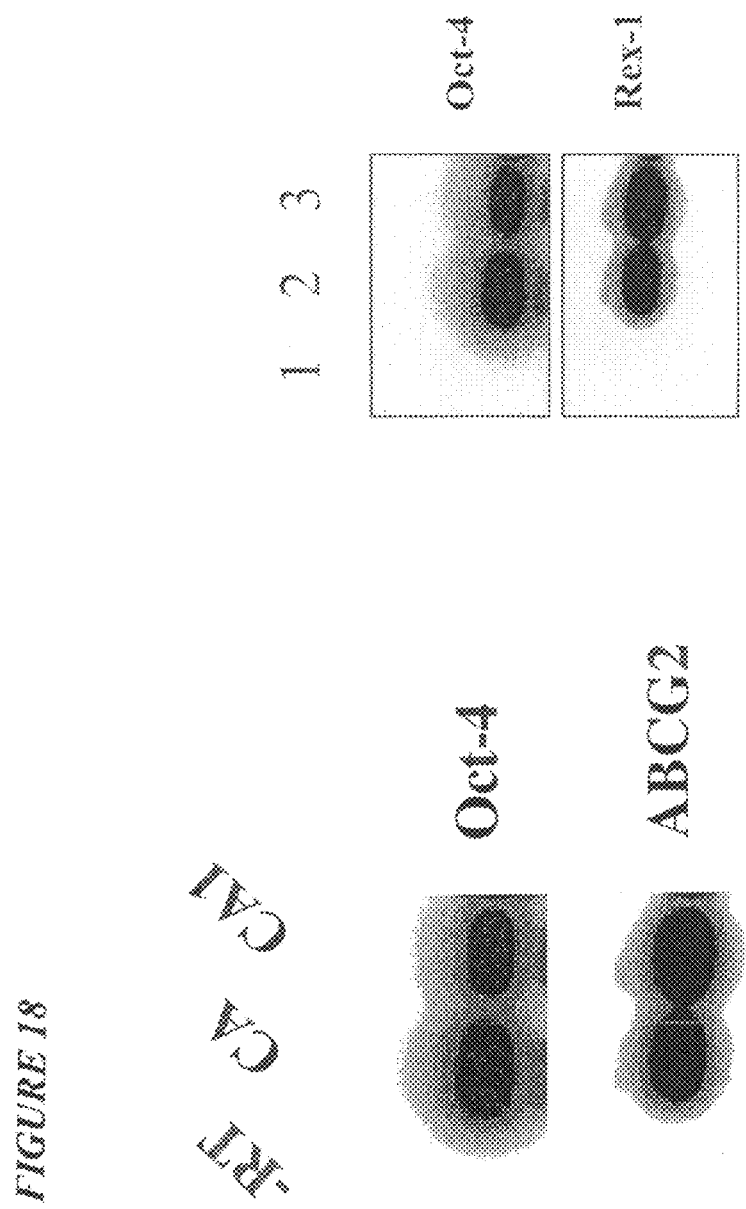

FIG. 18: Expression of Oct-4, Rex-1 and ABCG2 in CA stem cells:

Left hand side photos: Expression of Oct-4 and ABCG2 RNA in CA cells and clone CA1.

RNA are extracted from CA and CA1 cells and the expression of Oct-4 and ABCG2 is:

amplified by RT-PCR
then detected by hybridization.

Right hand side photos: Expression of Rex-1 transcription factor by Primo 2CA cells after 80 and 160 population doublings. The transcription factor Rex-1 is involved in maintaining the undifferentiated state of embryonic stem cells. The numbers "1", "2" and "3" mean "–RT (negative control)", "CA cells", and "CA1cells", respectively.

The PCR conditions are:
for Oct-4: 94° C., 1 min; 57° C., 1 min; 72° C., 1 min for 45 cycles.
Primers: 5'-GACAACAATGAAAATCTTCAGGAGA-3' (SEQ ID NO:1) and 5'-TTCTGGCGCCGGTTACA-GAACCA-3' (SEQ ID NO:2),
internal primer 5'-CACTCGGTTCTCGATACTGG-3' (SEQ ID NO:3) for a 220-bp fragment
for ABCG2: 94° C., 1 min; 60° C., 1 min; 72° C., 1 min for 31 cycles,
Primers: 5'-GGCCTCAGGAAGACTTATGT-3' (SEQ ID NO:4) and 5'-AAGGAGGTGGTGTAGCTGAT-3' (SEQ ID NO:5)

for Rex-1: 94° C., 1 min, 60° C. 1 min, 72° C. 1 min, Number of cycles 31; 72° 5 min, 1 cycle Primer: 5'-CTCTCCAGTATGAACCAGG-3' (SEQ ID NO:6) and 5'-GAAAGGATCAGAACAACAGC-3' (SEQ ID NO:7), internal primer, 5'-GGCATTGACCTATCAGATCC-3' (SEQ ID NO:8) for a 400-bp fragment.

FIG. 19: Schematic representation of a preferred variant of the method for producing adult stem cells from human adipose tissue.

Figure 20:
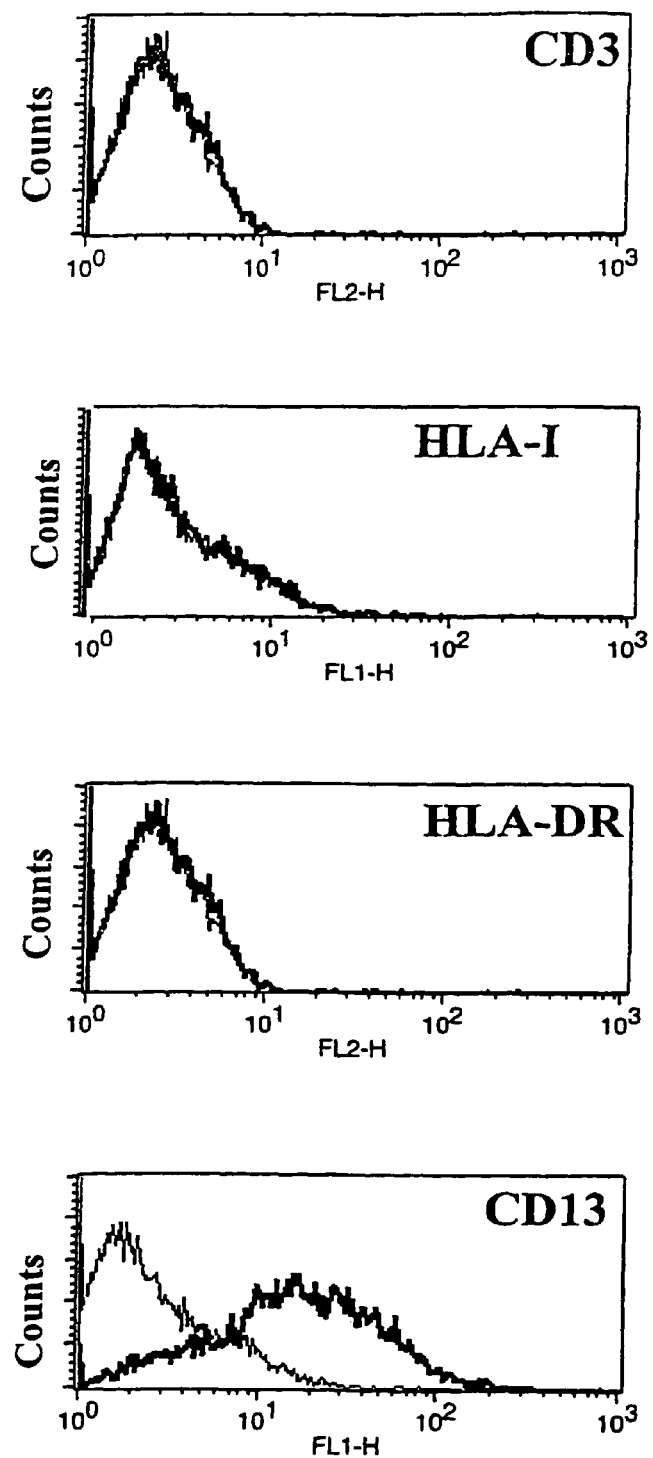

FIG. 20: Characteristics of Primo2 CA cells in terms of surface markers.

Primo2 CA cells at the 80, 120 and 160 population doubling stages were labelled with anti-HLA I, anti-HLA-DR anti-CD3, anti-CD13 antibodies previously coupled with FITC or phycoerythrin. Control=IgG; the following antibodies were used: HLA class I conjugated with fluorescein (FITC); HLA-DR (HLA class II) conjugated with phycoerythrin (PE); CD3 (marker for T lymphocytes) conjugated with PE; CD13 (markers for stromal cells of bone marrow, endothelial cells, early progenitors of granulocytes/monocytes and their descendance) conjugated with FITC.

Thin line: IgG control
Thick line: antibody of interest.

Figure 21:
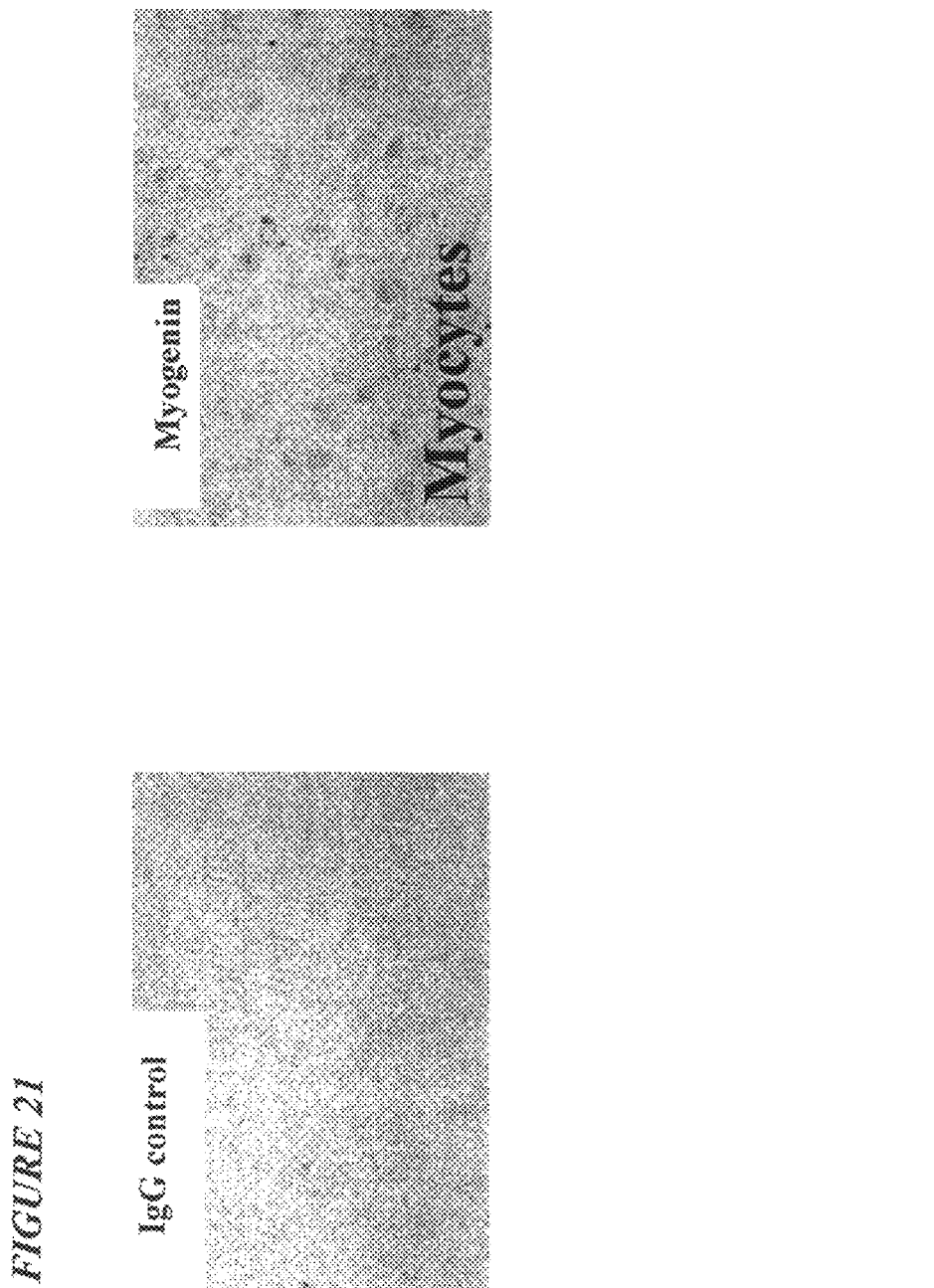

FIG. 21: In vitro myocyte differentiation after 4 days.

Detection by immuno-histochemistry of myogenin, an early factor in myocyte differentiation. FIG. 21 illustrates micrographs of Primo2 CA cells at 150 population doublings after 4 days in the presence of myocyte differentiation medium. The cells are fixed with 4% paraformaldehyde for 10 minutes at ambient temperature and permeabilized in the presence of PBS/0.1% Triton X100 for 10 minutes; the enodogenous peroxidase activity is then blocked by incubating the cells with 3% $H_2O_2$ for 5 minutes. The cells are then incubated with the primary antibody: anti-myogenin antibody (mouse anti-human IgG) (1:100) between 30 minutes and one hour at ambient temperature then with secondary antibody (anti-mouse IgG coupled with peroxydase).

Figure 22:
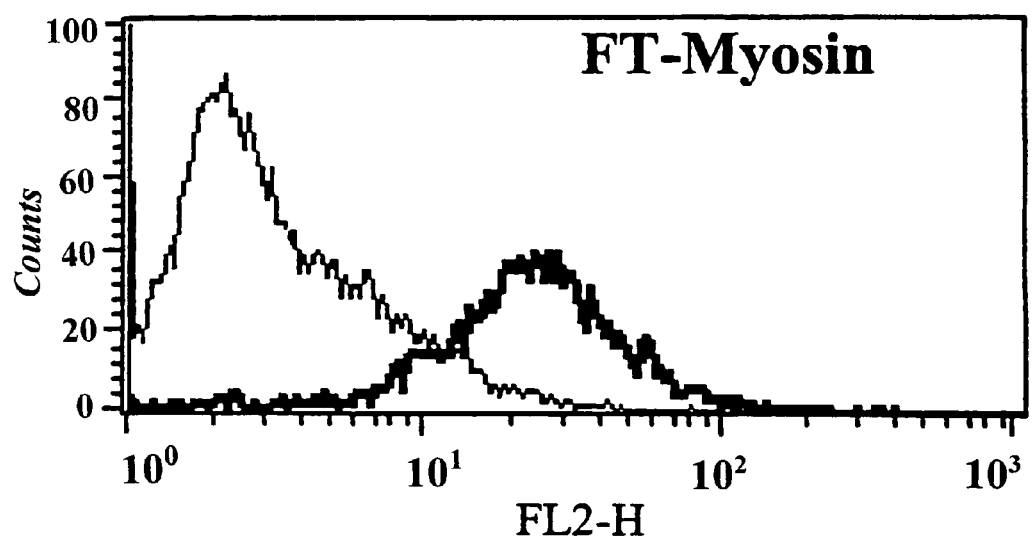

FIG. 22: In vitro myocyte differentiation after 21 days.

After 21 days in the presence of myocyte differentiation medium, the fast twitch myosin or FT myosin, a late marker for myocyte differentiation (intracellular marker) was detected. Detection by FACS: after detaching the Primo2CA cells (150 population doublings), they are fixed in the presence of PBS/1% formaldehyde for 15 minutes at ambient temperature then permeablized with a digitonin solution (10 µg/ml of PBS) for 7 to 8 minutes at ambient temperature. Antibody labeling is then carried out using the protocol described for expression of surface markers (FIG. 20). The antibody used is a mouse antibody directly conjugated to phycoerythrin and recognizing human FT myosin.

Thin line: IgG control
Thick line: FT-myosin

Figure 23:
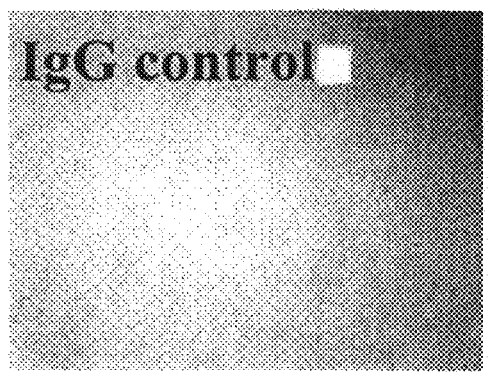
Figure 23:
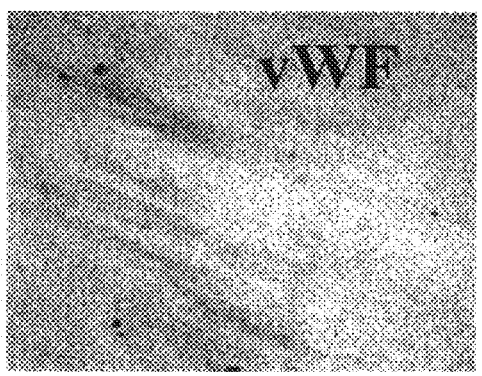

FIG. 23: In vitro differentiation of endothelial cells

Detection of von Willebrandt factor (vWF), a specific marker for endothelial cells, by immuno-histochemistry. FIG. 23 illustrates the expression of vWF by Primo2 CA cells at 150 population doublings after 21 days in the presence of angiogenic medium. The cells are fixed with 4% paraformaldehyde for 10 minutes at ambient temperature and permeabilized in the presence of PBS/0.1% Triton X100 for 10 minutes; the enodogenous peroxidase activity is then blocked by incubating the cells with 3% $H_2O_2$ for 5 minutes. The cells are then incubated with the primary antibody: anti-vWF (goat IgG recognizing both human, rat and mouse vWF) between 30 minutes and one hour at ambient temperature then with secondary antibody, anti-goat IgG coupled with peroxydase (1:100). After maintaining for 21 days in a medium composed of DMEM and hVEGF121 (10 ng/ml), the Primo2CA cells express vWF.

FIGS. 24 to 27: In vivo muscle regenerating power of Primo 2CA cells after 10 days, 50 days, 80 days and 6 months transplantation in the mdx mouse with no immunosuppressor: FIGS. 24, 25, 26 and 27 illustrate co-localization of human nuclei with the muscle fibers re-expressing dystrophin 10 days (FIG. 24), 50 days (FIG. 25), 80 days (FIG. 26) and 6 months (FIG. 27) after transplantation of Primo 2CA cells into the Tibialis Anterior. This co-localization was carried out by double labelling dystrophin by immunofluorescence and human nuclei by FISH. The transplanted cells are Primo 2CA cells at 160 population doublings, 150 000 in number.

The dystrophin immunofluorescence detection step was carried out before labelling the human nuclei by FISH:

Detection of dystrophin by immunofluorescence: the muscle sections are incubated for one hour with an antibody recognizing human dystrophin, previously coupled with fluorescein. The antibodies used are as follows:

either an antibody specific for human and mouse dystrophin (mouse anti-human IgG1: NCL-DYS2 from Novocastra, directed against the C-terminal end of human and mouse dystrophin) or, an antibody specific for human dystrophin (mouse anti-human IgG2a: NCL-DYS3 from Novocastra, directed against the N-terminal end of human dystrophin)

Detection of human nuclei by FISH: The probe used to detect the human nuclei is a specifc probe for human centromers (α-Satellite) coupled with digoxigenin (CP5095-DG.5, Appligene Oncor). The detection step consists of applying an anti-digoxigenin antibody coupled with rhodamine to slides. Before analysing the sections, the nuclei are completely stained using a DAPI solution (blue stain). The slides are then observed under a fluorescence microscope (Axiophot Zeiss) with a 100 watt bulb and a system of filters (Perceptive Scientific International).

| | |
|---|---|
| Green: | dystrophin; |
| Red: | human centromers |
| Blue: | nuclei (human and murine) |
| TA: | Tibialis Anterior |
| G: | Gastrocnemius |

Figure 24:
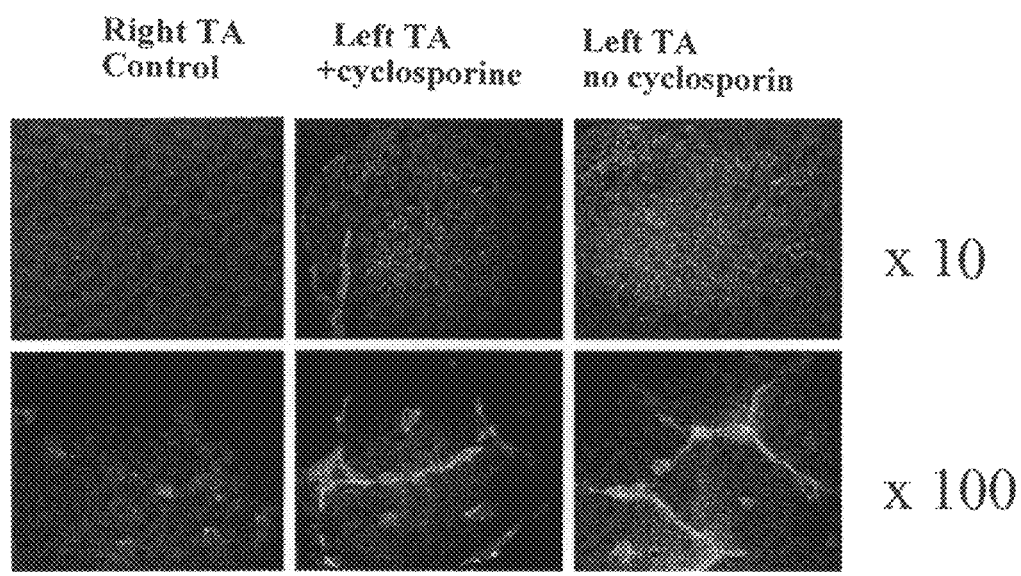
Figure 25:
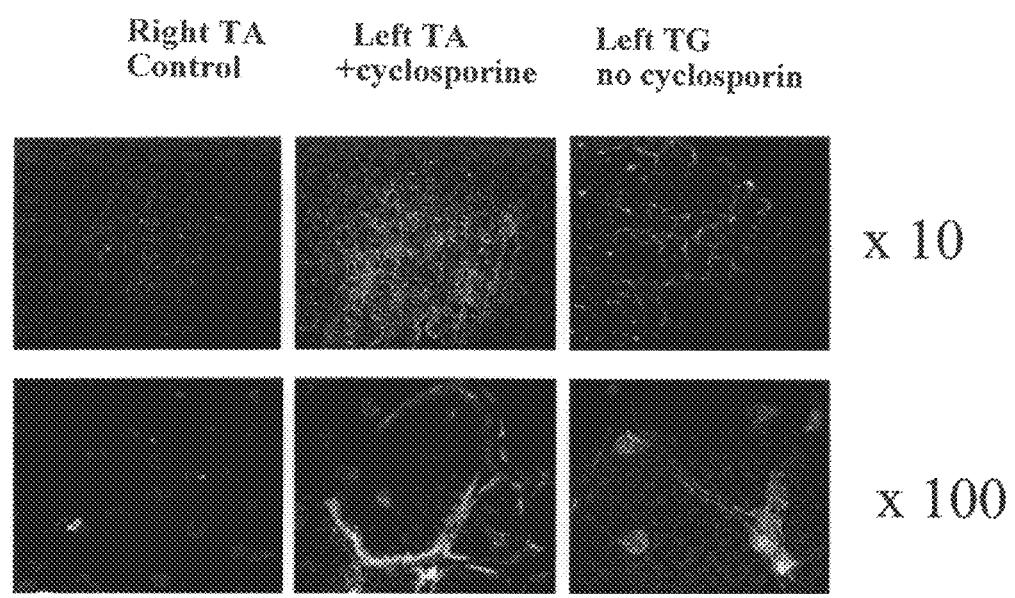
Figure 26:
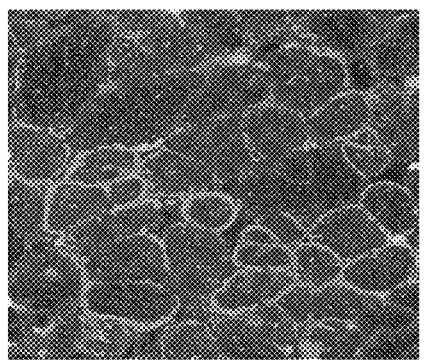
Figure 26:
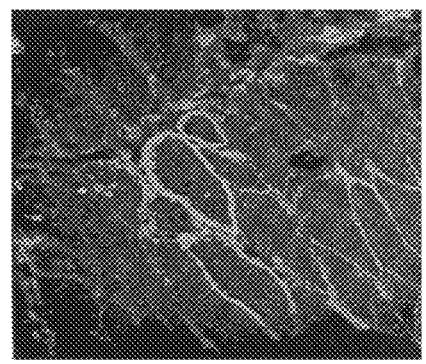
Figure 27:
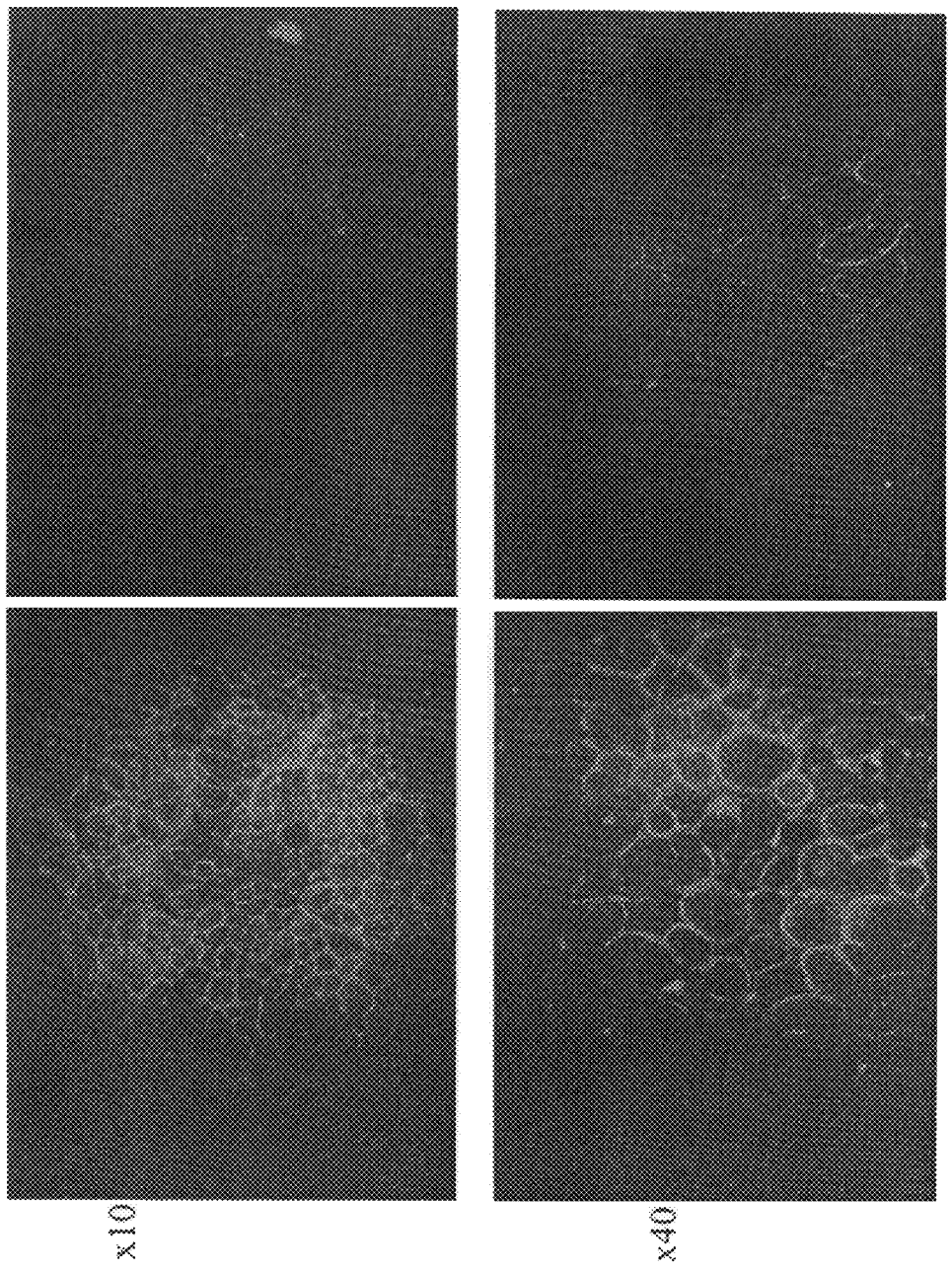

FIG. 24 (10 days): anti-dystrophin antibody: NCL-DYS2
Left Hand Side photos: untreated Tibialis Anterior (control);
Center photos: Tibialis Anterior of a mdx mouse treated with cyclosporin, 10 days after transplantation;
Right Hand Side photos: Tibialis Anterior of an immunocompetent mouse (no cyclosporin), 10 days after transplantation;

FIG. 25 (50 days): anti-dystrophin antibodies: NCL-DYS2
Left Hand Side photos: untreated Tibialis Anterior (control);
Center photos: Tibialis Anterior of a mdx mouse treated with cyclosporin, 50 days after transplantation;
Right Hand Side photos: Gastrocnemius of an immunocompetent mdx mouse (no cyclosporin), 50 days after transplantation, in adjacent TA;

FIG. 26 (80 days): anti-dystrophin antibodies: NCL-DYS2
Left Hand Side photos: Tibialis Anterior of an immunocompetent mdx mouse (no cyclosporin) 80 days after transplantation;

Right Hand Side photos: Gastrocnemius of an immunocompetent mouse (no cyclosporin), 80 days after transplantation, in adjacent TA;

FIG. 27 (6 months): anti-dystrophin antibodies: NCL-DYS2

Left Hand Side photos: Tibialis Anterior of an immunocompetent mdx mouse (no cyclosporin), 6 months after transplantation;

Right Hand Side photos: Tibialis Anterior of an untreated mouse (reference).

FIG. 28: Demonstration by comparative immunodetection of the human origin of the dystrophin expressed in the myofibers of transplanted muscle: An analysis of the presence of myofibers expressing dystrophin and the subcellular localization in the tibialis anterior 10 days after transplantation was carried out using the following antibodies:

(a): an antibody directed against the C-terminal end of human and mouse dystrophin (mouse anti-human IgG1: NCL-DYS2 from Novocastra,), (b) and (c): an antibody directed against the N-terminal end of human dystrophin (mouse anti-human IgG2a: NCL-DYS3 from Novocastra,), (d) and (e): an antibody specific for mouse collagen III.

Figure 28B:
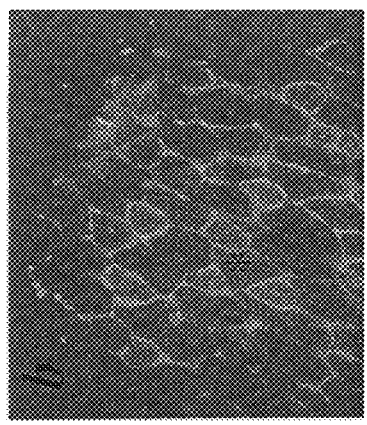
Figure 28A:
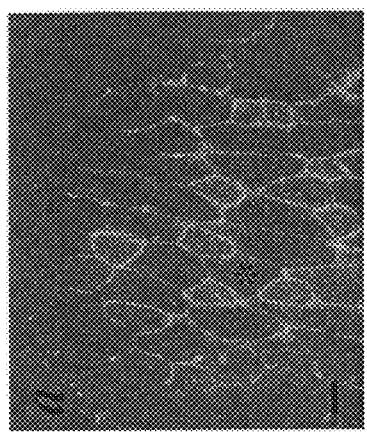
Figure 28D:
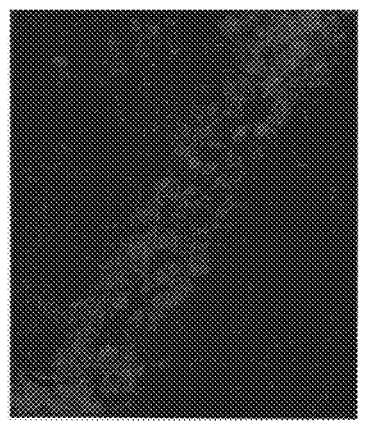
Figure 28E:
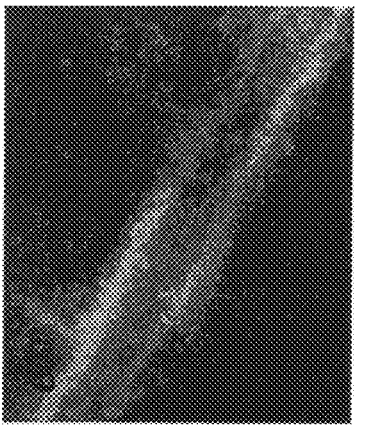
Figure 28C:

The scale bar corresponds to 15 µm in FIGS. 28(a) and 28(b), and to 1 µm in FIGS. 28(c) to (e). A star * indicates a section from the same myofiber.

The similarity between FIGS. 28(a) and (b) indicates the human origin of the expressed dystrophin. The human dystrophin is located beneath the sarcolemma. In contrast, the mouse collagen mi is present in the extracellular space between the myofibers (FIGS. 28(c) to (e)).

Figure 29A:
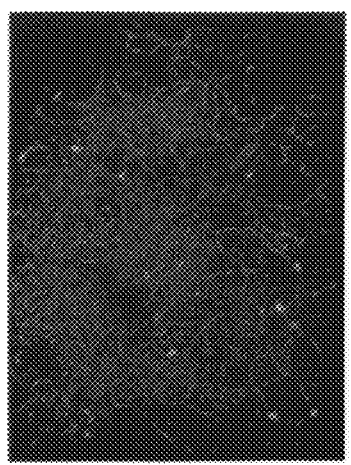

FIG. 29: Absence of cellular and humoral immune reactions 10 days after transplantation of the stem cells of the invention: The existence of any lymphocyte infiltration following transplantation of Primo 2CA cells into an immunocompetent mdx mouse was studied using hematoxylin (FIGS. 29(a), (b) and (c)), or mouse anti-CD3 antibody (FIGS. 29(a'), (b') and (c')).

Figure 29B:
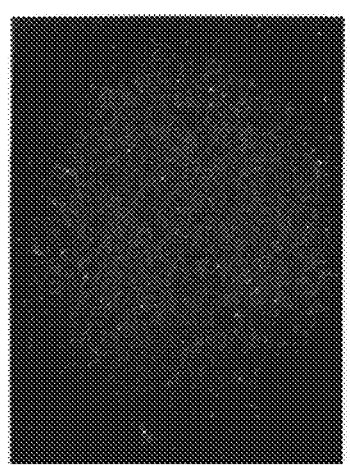
Figure 29C:
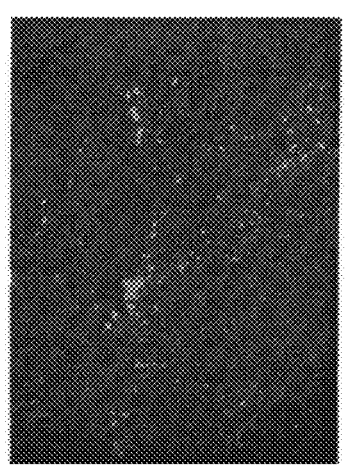

FIGS. 29(a) and (a'): Tibialis anterior of untreated mdx immunocompetent mouse (control);

FIGS. 29 (b) and (b'): Tibialis anterior of mouse, 10 days after transplantation of Primo 2CA cells, 150,000 in number;

FIGS. 29 (c) and (c'): Tibialis anterior of mouse, 10 days after transplantation of unpurified human stromal-vascular cells isolated from adipose tissue;

The scale bar corresponds to 50 µm in FIGS. 29(a) to (c), and to 20 µm in FIGS. 29(a') to (c').

10 days after transplantation of the Primo 2CA cells, no lymphocyte infiltration (CD3+) is observed (see FIGS. 29(b) and (b'), compared with FIGS. 29 (a) and (a')). In contrast, transplantation of unpurified stromal-vascular cells isolated from human adipose tissue induced a cytotoxic and humoral reaction (FIGS. 29(c) and (c')).

Figure 30:
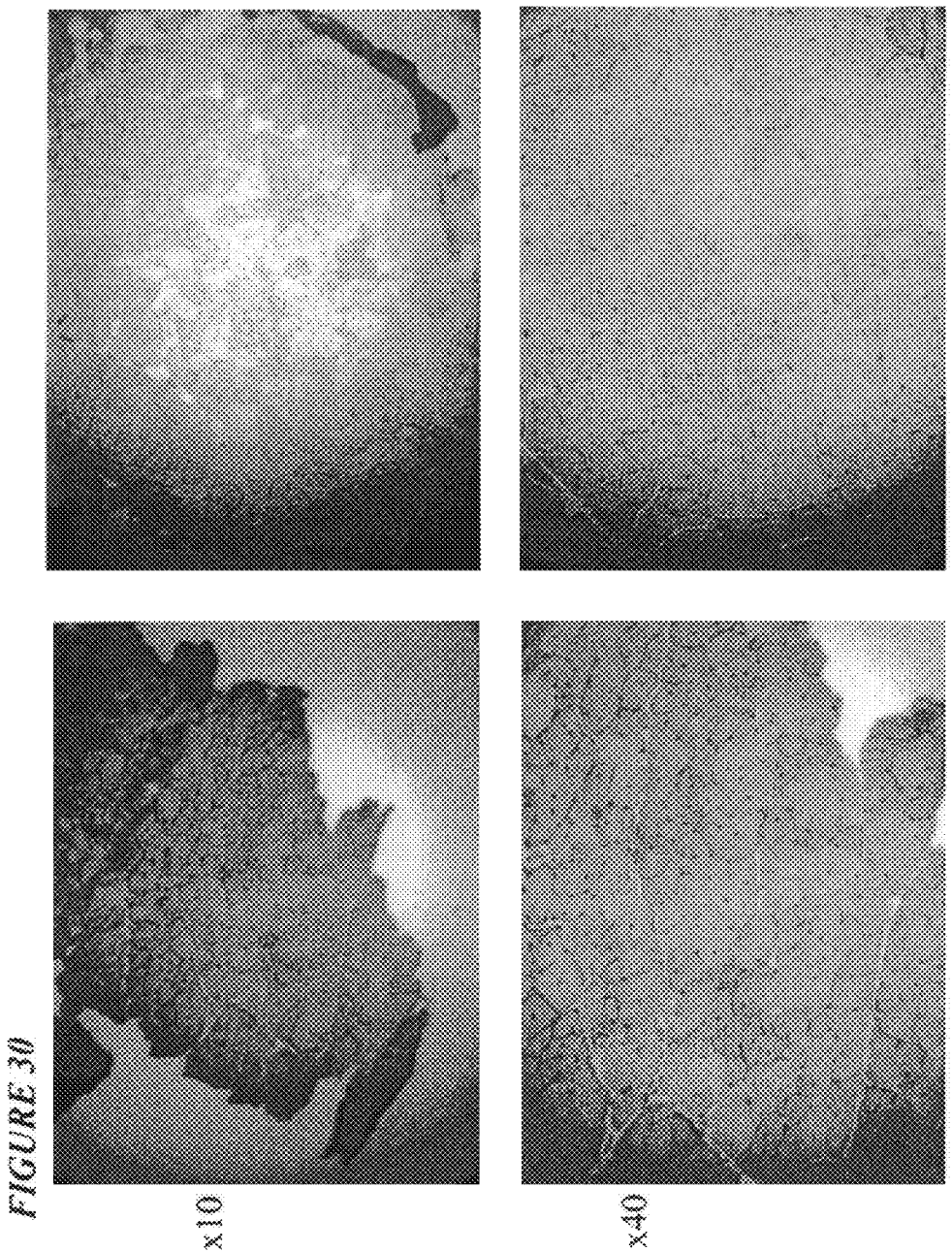

FIG. 30: Absence of cellular and humoral immune reactions 6 months after transplantation of Primo 2CA cells: The existence of a possible immune reaction 6 months after transplantation of Primo 2CA cells into a mdx immunocompetent mouse was studied by application of the same techniques as those described for FIG. 29.

Left Hand Side photos: Tibialis Anterior of mdx immunocompetent mouse, 6 months after transplantation of Primo 2CA cells, labelling with hematoxylin;

Right Hand Side photos: Tibialis anterior of mdx immunocompetent mouse, untreated (control), labelling with hematoxylin.

The absence of infiltration by CD3+ T lymphocytes was determined in the muscle transplanted with the Primo 2CA cells, signifying the absence of a rejection reaction 6 months after transplantation.

Figure 31:
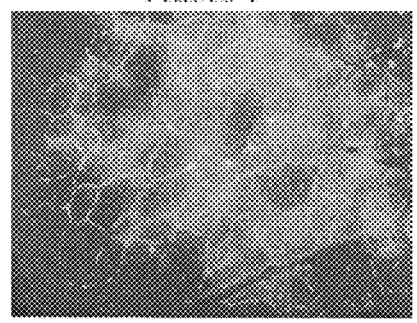
Figure 31:
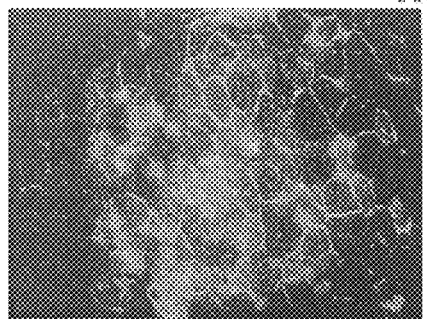
Figure 31:
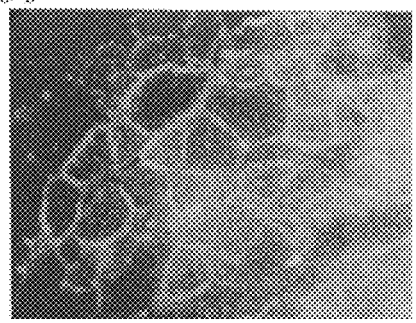

FIG. 31: In Vivo Muscle Regeneration Power of Primo1CA Cells and Primo 3 CA Cells 10 Days after Transplantation without Immunosuppressor into the mdx Mouse:

The in vivo muscle regeneration capacity was evaluated by co-localisation of human nuclei with muscle fibers re-expressing dystrophin. The co-localisation technique is identical to that described for the Primo 2CA cells (see legends to FIGS. 24 to 27), but the transplanted cells are Primo 1CA or Primo 3CA cells.

photo PRIMO1: Tibialis Anterior of an mdx immunocompetent mouse (no cyclosporin), 10 days after transplantation of Primo 1CA cells at 50 and at 120 population doublings, 150 000 in number. The antibody used to detect the dystrophin is an antibouy specific for human dystrophin (mouse anti-human IgG2a: NCL-DYS3 from Novocastra, directed against the N-terminal end of human dystrophin)

PRIMO3 photos: Tibialis Anterior of an mdx immunocompetent mouse (no cyclosporin), 10 days after transplantation of Primo 3CA cells at 45, 80 and 110 population doublings, 150 000 in number. The antibody used to detect the dystrophin is also NCL-DYS3 from Novocastra.

After 10 days of transplantation, a potential for muscle regeneration was visible, both for the Primo 1 CA cells and for the Primo 3 CA cells.

Figure 32:

FIG. 32: Absence of Cellular and Humoral Immune Reactions 10 Days after Transplantation of Primo 3 CA Cells:

The existence of a possible immune reaction 10 days after transplantation of Primo 3CA cells in an immunocompetent mdx mouse was studied by applying the same techniques as those described for Primo 2CA cells (see legends to FIGS. 29 and 30).

Primo 3 photo: Tibialis anterior of mdx immunocompetent mouse, 10 days after transplantation of Primo 3CA cells (110 population doublings, 150 000 in number), labeling with hematoxylin.

An absence of lymphocyte infiltration is observed with the Primo 3CA cells, suggesting behavior identical to that of the Primo 2CA cells.

EXAMPLES

1—Method for Obtaining and for In Vitro Expansion of Multipotent Stem Cells from Adipose Tissue 1.1. Description of Adipose Tissue Samples Obtained Six samples of adipose tissue were obtained from young children aged 1 month to 7 years; the sexes and anatomical locations were different.

Table I shows the origin of each sample, the weight thereof and the number of cells obtained using the technique described below.

TABLE I

Human adipose tissue samples used for the production of multipotent stem cells

| Sample name | Sex | Age | Anatomical location | Sample weight | Number of cells obtained |
|---|---|---|---|---|---|
| Primo 1 | F | 2 years 7 months | Umbilical region | 300 mg | 400 000 |
| Primo 2 | M | 5 years | Pubic region | 400 mg | 500 000 |
| Primo 3 | M | 4 months | Prepubic region | 210 mg | 400 000 |
| Primo 4 | F | 7 years | Inguinal region | 2.1 g | 2 000 000 |
| Primo 5 | M | 1 month | unknown | 200 mg | 1 000 000 |
| Primo 6 | M | 18 months | unknown | 200 mg | 350 000 |

The Examples below describe obtaining multipotent stem cells from samples Primo 1 to 6. Said stem cells were obtained by carrying out the following steps:
- isolating multipotent cells from the sample
- in vitro enriching of the cell culture in multipotent cells
- obtaining a population of quiescent stem cells
- inducing intensive proliferation of stem cells The stem cells obtained were characterized by
- measurement of telomerase activity
- producing Karyotypes at different passage
- studying cell plasticity (differentiation into different cell types)
- determining presence or absence of cell markers
- cloning stem cells The methodology and results are described in detail below.

1.2 Method for Isolating Multipotent Cells from the Adipose Tissue of Young Children After surgery, the sample is stored in DMEM medium (Dulbecco's Modified Eagle's Medium). +10% foetal calf serum, at ambient temperature. The tissue is rinsed in PBS (Phosphate Buffer Saline) at 37° C. then drained and weighed. The sample is then very finely chopped to optimize the enzymatic digestion step.

The digestion medium is composed of DMEM medium (Dulbecco's Modified Eagle's Medium) containing antibiotics (100 U/ml of penicillin and 100 μg/ml of streptomycin), 2 mg/ml of collagenase (Boerhinger reference 103586) and 20 mg/ml of bovine serum albumin fraction 5 (Sigma A reference 2153). The digestion volume isa function of the tissue weight; generally, 1 ml of digestion medium for 100 to 200 mg of tissue. Digestion is carried out at 37° C. under gentle agitation. In contrast to conventional techniques for the preparation of human preadipocytes, the digestion period is very rapid, 5 to 10 minutes, which corresponds to complete dissociation of the tissue by the collagenase. The collagenase activity is then inhibited by adding foetal calf serum (200 μl/ml of digestion medium).

The cell preparation is then centrifuged for 5 min at 1000 rpm, a step which enables the separation of the adipocytes (which float) from other cell types contained in the adipose tissue (pre-adipocytes, stem cells, endothelial cells, pericytes, mastocytes . . . ). It is important to note that this step in the procedure is carried out without filtration, which means that all of the cell types contained in the adipose tissue are preserved (with the exception of the adipocytes).

The cell pellet obtained after centrifuging is re-suspended in the culture medium: DMEM+decomplemented foetal calf serum+antibiotics (100 U/ml of penicillin, 100 μg/ml of streptomycin). The number of cells obtained is counted. The cell yield varies depending on the samples 1000 to 5000 cells per mg of tissue. The cells are seeded at high density, 1000 to 3000 cells per cm into plastic dishes (crystalline polystyrene, Greiner).

When put into culture, two cell sub-populations are isolated according to their adhesion rates. The first sub-population, designated "CA", is constituted by cells which adhere very rapidly (less than 12 h). The second sub-population, CS, is constituted by cells that adhere much more slowly (48 to 72 h).

In practice, 12 h after starting the culture, certain cells have adhered to the plastic. Those cells constitute the CA population. The cells constituting the CS population are at the same moment in suspension in the culture medium. That culture medium is removed and deposited in a new culture dish. After 72 h, the CS cells have adhered.

1.3 Enriching the Culture in Multipotent Stem Cell

1.3.1 Obtaining a Population of Quiescent Stem Cells

The two sub-populations, CA and CS, are maintained in culture in the same way. Said cells, in the early stages (corresponding to about 50-60 population doublings) have similar characteristics in terms of plasticity, proliferation and morphology.

The cells are maintained in the culture medium DMEM+ 10% decomplemented foetal calf serum+antibiotics (100 U/ml of penicillin, 100 μg/ml of streptomycin).

When the cells reach 80% confluence, they are treated with trypsin (Trypsine-EDTA, Invitrogen) and taken up into culture in three new dishes of identical diameter. The seeding density corresponds to 1000 to 3500 cells/cm². The cells are deliberately not diluted further to preserve the multipotent cells, which theoretically divided more slowly than the precursors, in all of the dishes.

The cells were maintained under these conditions until they stop proliferating. For Primo 2, the CA and CS cells stop proliferating after cell transfer 20 (T20) corresponding to 60 population doublings.

Xgal staining (revealing the endogenous β-galactosidase activity detected at pH 6 and demonstrating cell senescence) revealed that the CS population was senescent while the CA population was simply quiescent (see FIG. 1).

For this enrichment step, different culture media were tested. It was observed that the stem cells of the invention did not react to "Leukemia Inhibitory Factor" (LIF) (10 ng/ml). LIF produces no change in the morphology or proliferation of the cells. This tends to confirm that the cells do not express the LIF receptor (LIF-R⁻).

1.3.2 Induction of Intensive Stem Cell Proliferation

After establishing a population of quiescent CA cells, human bFGF (basic Fibroblast Growth Factor) is added to the culture medium described above in a concentration of 5 ng/ml of medium.

As indicated in FIG. 2, only cells of the CA population effectively respond to bFGF. In contrast, bFGF had practically no effect on the CS population at late stages (i.e. after 50 population doublings).

These observations confirm once again the quiescent state of the CA population and the senescent state of the CS population.

The CA cells, treated with bFGF, are subjected to trypsin treatment at 80% confluence, this time diluted 5 to 10 times in new identical culture dishes.

Two supplemental points can be made regarding bFGF:
bFGF causes a change in the morphology of the cells. When quiescent, they are flattened and enlarged. In the presence of bFGF, and thus in the proliferative phase, they take on a fibroblast form (FIG. 3, FIG. 12)
further, the effect of bFGF is reversible (FIG. 3).

1.4. Freezing Cells from the Two Sub-Populations CA and CS

Cells from the two sub-populations CA and CS are frozen regularly to constitute a stock of each cell population and to allow its development during cell transfers to be followed. Cryoconservation does not change the properties of said cells.

In practice, the cells were trypsinated, centrifuged and re-suspended in a freezing medium constituted by foetal calf serum supplemented with 10% DMSO. These cells were then placed at −20° C. for 1 h then at −80° C. overnight and finally stored in liquid nitrogen at −180° C.

2. Measurement of Telomerase Activity of the Stem Cells

2.1 Methodology for Determining Telomerase Activity

The telomerase activity is quantified using a TeloTAGGG Telomerase PCR Elisa$^{PLUS}$ kit (Roche).

The telomerase activity is quantified in two steps:
i) The first step is an amplification/elongation step (or TRAP assay) wherein the telomerase adds telomeric motifs (TTAGGG) to the 3' end of a biotinylated primer.
ii) The second step is detection and quantification by Elisa.

The PCR products obtained in step 1 are hybridized with a specific primer for telomeric ends labeled with digoxigenin. Further, Elisa microplates were treated with streptavidin to immoblise the products via the biotin. The immobilized amplicons were detected with an anti-digoxigenin antibody conjugated with an anti-DIG-HRP and the peroxidase substrate TMB.

The intensity of the photometric reaction was estimated using an Elisa microplate reader (absorbance at 450 nm with a reference wavelength of 690 nm).

The relative telomerase activity of the sample is then calculated with respect to the telomerase activity of a positive control (cells from the HEK293 line, Human Embryonic Kidney 293).

2.2 Results of Telomerase Activity Determination

Using the "TeloTAGGG telomerase PCR Elisa Plus" kit sold by Roche, the telomerase activity present in the 2 sub-populations CA and CS of Primo2 was quantified.

A significant telomerase activity was detected in the stem cells of the invention. For Primo 2CA (T25: cell transfer 25, corresponding to about 100 population doublings), the telomerase activity was about 20% compared with the telomerase activity of the transformed human line HEK293T (Human Embryonic Kidney 293 immortalized by T antigen). The HEK293T line is used in this kit as a reference.

In contrast, no significant telomerase activity was detected in the CS cells, for example the cells from Primo 2CS (T20) had an activity of about 5% compared with that of HEK293T.

3. Karyotype of Stem Cells

The karyotype allows observation and classification of the chromosomes present during metaphase.

3.1 Methodology for Determining Karyotype

Metaphases are obtained using conventional cytogenic techniques. After accumulating the cells in metaphase by blocking the fusorial apparatus (incubation in the presence of colchicine for 3 h), chromosome dispersion is carried out in the cytoplasm by the action of a hypotonic solution (75 mM KCl for 40 min at 37° C.) followed by fixing with methanol/acetic acid (3/1). The chromosomes are then identified using RHG-banding techniques.

3.2 Results of Karyotype Determination

The cell karyotype was determined. These karyotypes were carried out on the 2 sub-populations CA and CS in the presence or absence of bFGF and at different passages (T21, T23 and T34 for Primo 2CA).

In all cases, the karyotypes were completely normal. Thus, the cells had not undergone any chromosomal rearrangement. FIG. 4 shows the karyotype of Primo 2CA cells.

4. Cell Plasticity of the Stem Cells

Stem cell plasticity is evaluated using the following techniques:

4.1 Methodology for Evaluating Cell Plasticity

4.1.1. Conditions for Differentiation into Different Cell Types

The cells are trypsinated then seeded at 20000 cells/cm$^2$. The cells reach confluence 24 to 48 hours later. As confluence is a critical step for differentiation, the cells are maintained at confluence for an additional 24 h before proceeding to differentiation (adipocytes, osteoblasts, myocytes).

i) Conditions for Differentiation into Adipocytes

The confluent cells are incubated in a DMEM/Ham's F12 (vol/vol, 1:1) medium supplemented with 100 U/ml of penicillin, 100 μg/ml of streptomycin, 5 μg/ml of human insulin (Sigma), 10 μg/ml of human transferrin (Sigma), 1 μM of PPAR activator (for example BRL49653), 100 to 250 μM of isobutyl-methylxanthine (IBMX) and 1 μM of dexamethasone. 48 to 72 hours later, this medium is replaced by the medium described above but containing no IBMX and dexamethasone. This differentiation medium is replaced every 2-3 days for a period of 15 to 20 days corresponding to an optimum adipocyte differentiation.

ii) Conditions for Differentiation into Osteoblasts

Cells that have been confluent for 24 h are incubated with an osteoblast differentiation medium composed of DMEM, 100 U/ml of penicillin, 100 μg/ml of streptomycin, 10% of decomplemented foetal calf serum, 0.1 μM of dexamethasone (SIGMA), 10 mM of β-glycerophosphate (SIGMA) and 50 μM of ascorbic acid (SIGMA).

The medium is replaced every 2-3 days over a period of 15 to 20 days.

iii) Conditions for Differentiation into Myocytes

Cells that have been confluent for 24 h are incubated either in DMEM medium or in PromoCell medium in the presence of 2% of decomphmented foetal calf serum and antibiotics (100 U/ml of penicillin, 100 μg/ml of streptomycin). The medium is replaced every 2-3 days over 3 to 6 weeks particularly every 3 days over 21 days.

iv) Conditions for Differentiation into Endothelial Cells

The cells are seeded at 20 000/cm$^2$ in a DMEM medium containing 10 ng/ml of human $VEGF_{121}$ (SIGMA). The differentiation medium is replaced every 2-3 days for 21 days.

4.1.2 Stains i) Oil Red O stain (Adipocytes: Staining of Intracellular Lipids)

After fixation in a PBS/0.25% glutaraldehyde solution, the cells are incubated for 5 minutes at ambient temperature in a solution of Oil Red O 2% (weight/volume). The cells are then washed and stored in 70% glycerol.

ii) Alizarin Red Stain (Osteoblasts: Calcification of Extracellular Matrix)

After fixation in a PBS/0.25% glutaraldehyde solution, the cells are incubated for 5 minutes at ambient temperature in a solution of Alazarin Red O 1% (weight/volume). The cells are then washed with water and stored dry.

4.1.3. Transcriptional Analysis i) Extraction d'RNA

Cellular RNAs are extracted using Tri Reagent (Euromedex, Ref TR-118)

ii) Northern Blot

20 µg of RNA/well are deposited on an agarose gel (1.2%)/MOPS (1×)/formaldehyde (1.1M). After electrophoresis in a MOPS (1×) migration buffer, the RNA is transferred to a membrane of nylon Hybond N+ (Amersham Pharmacia).

The membrane is then hybridized in the presence of a specific probe labelled with $^{32}P$ [dCTP] using the Rediprime™ II Random Prime Labelling system (Amersham Pharmacia).

iii) RT-PCR

Reverse transcription PCR reaction was carried out using a OneStep RT-PCR kit from Qiagen.

4.1.4. Analysis of the Expression of Intracellulars Markers

This technique was used to quantify the number of Primo2CA cells capable of in vitro differentiation into myocytes. The marker that was analysed was fast twitch myosin ou FT myosin, a late marker for myogenesis.

After detaching the cells, they are fixed in the presence of PBS/1% formaldehyde for 15 min at ambient temperature then permeabilized with a solution of digitonin (10 µg/ml of PBS) for 7 to 8 min at ambient temperature.

Antibody labeling is then carried out, using the protocol described for detecting surface markers (see Examples 7 and 11 below). The antibody used is a mouse antibody directly conjugated with phycoerythrin and recognizing human FT myosin.

4.1.5. Immunohistochemistry

The cells are fixed with 4% paraformaldehyde for 10 min at ambient temperature. When the desired protein is nuclear (such as myogenin, for example), the cells are permeabilized in the presence of PBS/0.1% Triton X100 for 10 min. The activity of the endogenous peroxidase is then blocked by incubating the cells with 3% $H_2O_2$ for 5 min.

The cells are then incubated with the primary antibody for between 30 min and 1 h at ambient temperature, then with the secondary antibody (anti mouse IgG coupled with peroxidase (Vector Laboratories) or anti-goat IgG coupled with peroxidase (Santa Cruz Biotechnology).

The primary antibody used in our experiments, von Willebrand factor (vWF) (goat IgG, recognizing both human, rat and mouse vWF) (Santa Cruz Biotechnology) and Myogenin (mouse anti human IgG) (Santa Cruz Biotechnology), were used in a proportion of 1:100.

4.2 Results of Cell Plasticity Analysis

4.2.1. Plasticity of the Two Cell Sub-Populations CA and CS at Early Passages At early stages (for example T1, T5, T7 corresponding to 3, 15 and 21 population doublings, respectively), the CA and CS populations have the same characteristics in terms of plasticity, morphology and proliferation.

i) Differentiation into Adipocytes

Figure 14C:
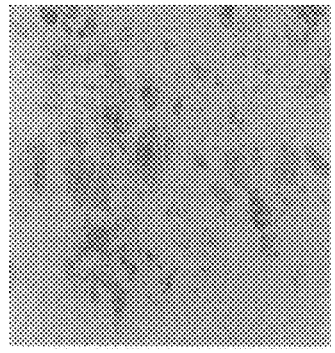
Figure 14B:
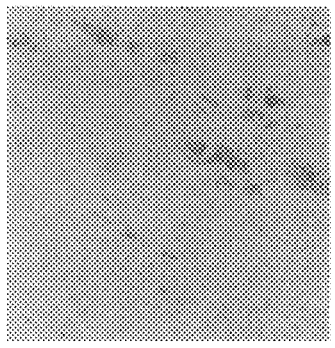
Figure 14A:
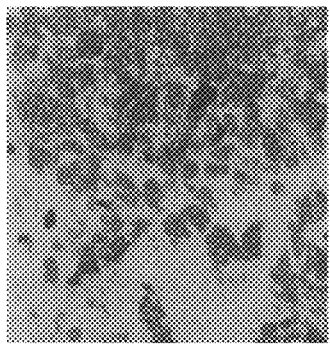

The results for the experiments involving Oil Red O staining are shown in FIG. 5 (for Primo 2CA and Primo 2CS) and FIG. 14 for Primo 1CA (40 population doublings), Primo 3CA (25 population doublings) and Primo 6CA (25 population doublings). Further, the adipocytes from Primo 1CA, Primo 3CA and Primo 6CA after 50, 40 and 40 population doublings, respectively, are shown in FIG. 13. A comparison of FIGS. 13 and 14 clearly shows that the higher the number of population doublings, the more homogeneous the differentiation.

A "Northern Blot" analysis (FIG. 6) demonstrates the transcriptional expression of adipogenic markers (aP2 and PPARγ2) during differentiation: CA T14 (42 population doublings) and CS T16 (48 population doublings).

ii) Differentiation into Osteoblasts

FIG. 7 shows the differentiation of CS and CA cells into osteoblasts. Alizarin Red stain.

4.2.2. Evolution of Cell Plasticity at Late Passages

Cells of Primo 2 CS, after transfer 20 (corresponding to about 60 population doublings) become senescent. They simultaneously lose their proliferative potential and their differentiation capacity.

In contrast, the cells of the CA population at the same stage become quiescent. They proliferate in the presence of bFGF and retain their plasticity. Said plasticity remains unchanged at transfer 40 (corresponding to about 200 population doublings). FIG. 8 shows adipocyte and osteoblast differentiation for Primo2 CA T30 (about 130 population doublings).

At late passages, the CA population also retains transcriptional expression of the different specific markers either for adipocyte differentiation, or for osteoblast differentiation. (FIG. 9) Primo2 CA T32 (140 population doublings).

4.2.3—Capacity of Primo2 CA Cells to Differentiate into Myocytes and Endothelial Cells In Vitro Under appropriate culture conditions, Primo 2CA cells are capable of differentiating in vitro after about 3 weeks into myocytes and endothelial cells.

i) Myocyte Differentiation

After 4 days in the presence of myocyte differentiation medium, Primo2CA cells express early markers for myocyte differentiation such as myogenin (inmmunohistochemical labeling, cf FIG. 21). After 7 days, myogenin expression is not longer detectable.

After 21 days, 95% of the Primo2 cells cultivated in this medium express a late marker for myocyte differentiation, namely Fast Twitch myosin (intracellular labeling and FACS analysis, cf FIG. 22).

ii) Differentiation into Endothelial Cells

In contrast to adipocytes, osteoblast and myocyte cells which belong to the "Limb bud mesoderm", endothelial cells derive from the visceral mesoderm. After being maintained for 21 days in a medium composed of DMEM and hVEGF121 (10 ng/ml), the Primo2 CA cells express von Willebrand factor, a specific marker for endothelial cells (immunohistochemistry, cf FIG. 23).

5. Characterization of Adipocyte Functionality by Enzymatic Assay

5.1 Methodology for Characterizing Adipocyte Functionality

5.1.1 Measuring Gycerophosphate Dehydrogenase Activity (GPDH)

Firstly, the cells which are to have the GPDH activity measure, are lysed. The principle of the assay can be summarized in the following scheme:

Dihydroxyacetone phosphate + NADH $\xrightarrow{GDPH}$ Glycerophosphate + NAD

The initial rate of disappearance of NADH is determined at 340 nm (in the presence of NADH, DHAP and cell lysate), which allows the quantity of degraded substrate and hence the specific enzymatic activity (after assaying the proteins) to be calculated. The reading is made with a spectrophotometer, allowing kinetic measurements to be carried out (KONTRON Uvicon 860 thermostatted at 37° C.).

5.1.2. Lipolysis Test

This test consists of measuring the radiolabelled glycerol liberated by adipocytes in the presence of adrenergic receptor agonists. The method used is that described by Bradley D C and Kaslow H R (Anal Biochem, 1989, 180, 11-16). The glycerol liberated is phosphorylated in the presence of glycerokinase and ATP and ATP labeled with $^{32}P$ in the α position. The residual ATP is then hydrolyzed in an acid medium at 90° C. and precipitated with ammonium molybdate and triethylamine. The radioactivity incorporated in the form of glycerophosphate labelled with $^{32}P$ is estimated by counting in a β counter and the values are expressed in pmol using a calibration curve.

5.2 Results of Characterization of Adipocyte Functionality

5.2.1. Glycerophosphate Dehydrogenase Activity (GPDH)

Primo 2CA cells (T24 in the presence of human bFGF):
After 11 days of differentiation (2 experiments)
Control: 77 nmol/min/mg of protein
In the presence of an agonist of PPARγ (BRL49653): 290 nmol/min/mg of protein
After 16 days of differentiation (3 experiments)
Control: 20 nmol/min/mg of protein
In the presence of an agonist for PPARγ (BRL49653): 390 nmol/min/mg of protein
Primo 2CS cells (T22 in the presence of human bFGF):
After 13 days of differentiation (3 experiments)
Control: 22 nmol/min/mg of protein
In the presence of an agonist for PPARγ (BRL49653): 30 nmol/min/mg of protein

5.2.2. Lipolysis Capacity of Primo 2CA Cells

Lipolyses were carried out on Primo 2CA T32 cells with specific agonists for the different β adrenergic receptors, namely:
Isoproterenol: β1, β2 adrenergic
Dobutamine: β1 adrenergic
Terbutaline: β2 adrenergic
CL316243 β3 adrenergic:
The following lipolysis rates were obtained (using a glycerol calibration curve):
Control: 5.76 nmol/h/mg of protein
Dobutamine: 60.1 nmol/h/mg of protein
Terbutaline: 93.78 nmol/h/mg: 60.1 nmol/h/mg of protein
CL316243: 17.1 nmol/h/mg of protein
The results are shown in FIG. 10.
The lipolysis experiments show the presence of β1 and β2 adrenergic receptors and the absence of β3 adrenergic receptors; these results are in accordance with in vivo observations (Galitzky et al; (1997) British J. Pharmacol 122: 1244-1250).

6. Characterization of Osteoblast Functionality by Detecting Calcium Associated with the Extracellular Matrix

6.1 Methodology for Characterizing Osteoblast Functionality

To detect the calcium secreted by osteoblasts, the cells were cultivated in the osteoblast differentiation medium described above.
After optimum differentiation, the cell mat is lysed with a 0.1 N NaOH solution for 45 min. A neutralization step is then carried out by adding 1N HCl (0.2 vol/1 vol of NaOH). The dishes in which the extracellular matrix remains are dried then incubated with the solution from a "SIGMA calcium detection kit". The quantity of calcium secreted by the osteoblasts is quantifed by measuring said solution using a spectrophotometer (DO575)

6.2. Results: Osteoblast Functionality

The functionality of the osteoblasts was demonstrated by the technique for detecting calcium associated with the extracellular matrix (FIG. 11).
We should also emphasize the importance of the batch of foetal calf serum in osteoblast differentiation. This reflects the crucial role in osteoblast differentiation of certain cytokines, hormones or growth factors that are not characterized and which are present in varying proportions depending on the serum batch.

7. Cell Labeling and Flow Cytometry Analysis

The HLA Class I negative nature of the stem cells of the invention was demonstrated by flow cytometry using a conventional single label system:

7.1 Single Labeling

The cells are detached then washed in PBS. After centrifuging, the cells are re-suspended and incubated with the primary antibody at a concentration of 10 µg/ml for 30 min at 4° C. The antibodies used are either monoclonal mouse antibodies directed against class I HLA molecules (W6/32, Novocastra), or a mouse IgG antibody (Santa Cruz) used as a negative control. The number of cells used for each condition is $5>10^5$ to $10^6$. The following cells were used for this analysis:

| | |
|---|---|
| HeLa: | Human tumor cells (positive HLA Class I: positive control). |
| SVF: | adult adipose tissue, no population doubling (positive HLA Class I) |
| Primo 2CA: | 120 population doublings |
| Primo 2CS: | 45 population doublings |

The cells are then washed and incubated for 20 min at 4° C. with an antibody (secondary) which is a mouse anti IgG antibody coupled with FITC (0.2 µg/$10^6$ cells) (Caltag).

The cells are then washed and their fluorescence analyzed by flow cytometry (Scan FACS Becton Dickinson).

Figure 15:
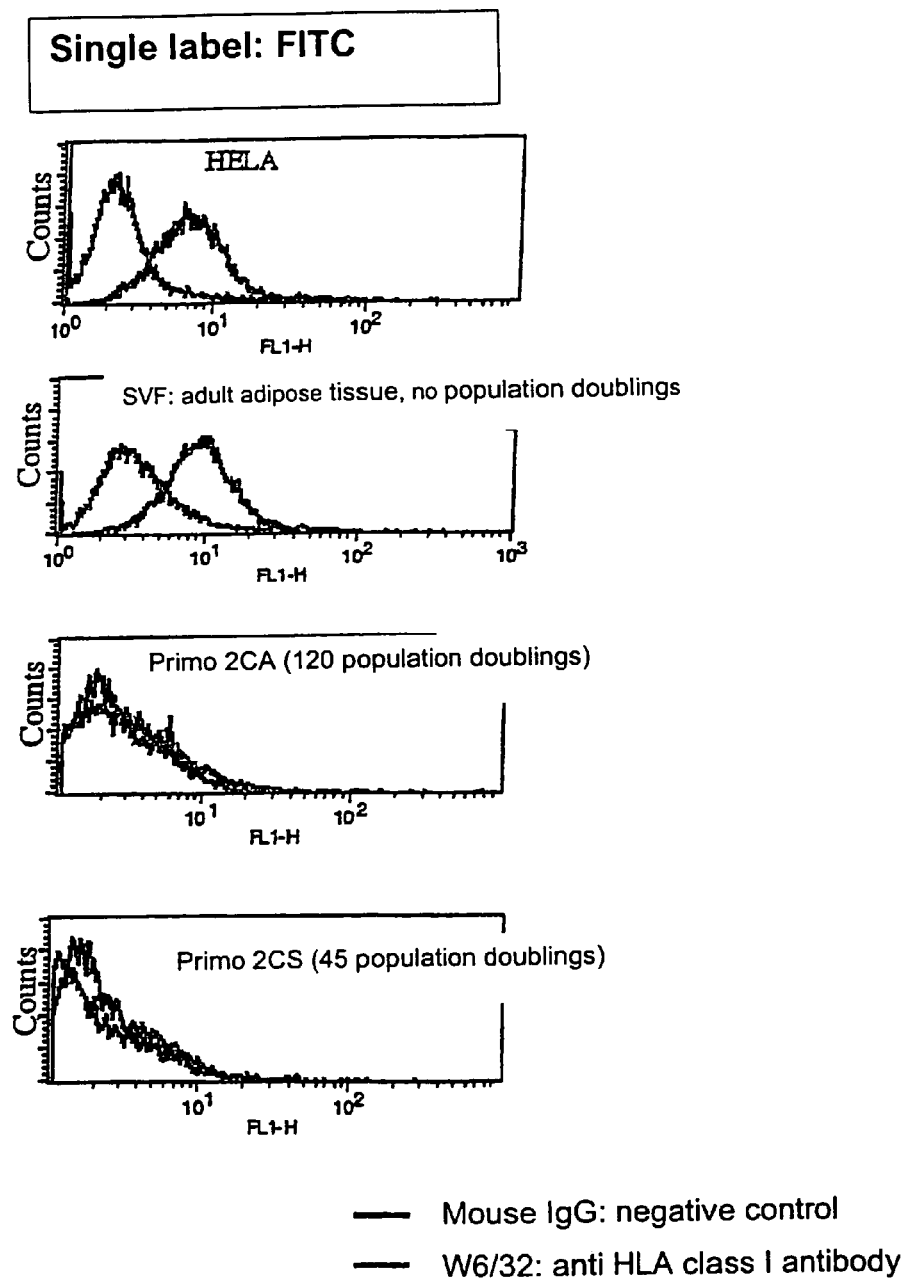

The results are shown in FIG. 15 and show that the stem cells of the invention (for example Primo 2CA) have a level of HLA class I molecule expression that cannot be detected by single label flow cytometry. The stem cells of the invention are thus "HLA class I negative".

This flow cytometry experiment was also carried out with stem cells from Primo1CA and Primo3CA and with cells from Primo2CS (FIG. 15). In all cases, surface expression of HLA class I was negative.

8. Obtaining Multipotent Clones from CA Cells

Primo 2CA cells were seeded in a limiting dilution condition, namely ⅓ of cells per well of 24 well plates, there maintained in the presence of 10% FCS containing 5 ng/ml bFGF.

Ten days later, the clones were isolated and amplified. These clones preserved their undifferentiated phenotype until made to differentiate. Their capacity for differentiation into adipocytes and osteoblasts was then demonstrated.

FIG. 16 shows two clones, CA1 and CA3, which were placed in a culture medium allowing differentiation into adipocytes and osteoblasts. The adipocytes were revealed by Red Oil stain and the osteoblasts were revealed by Alizarn red stain. The clones analyzed by flow cytometry were also revealed to be HLA class I and II negative.

9. Expression of a Transgene in Stem Cells

The stem cells of the invention, in particular cells from clone CA1 (obtained as described in Example 7), were transduced at the 21 population doublings stage by a retrovirus expressing a gene for antibiotic resistance, puromycin, and the reporter gene LacZ under the control of an LTR promoter.

The infectious virions were produced from 293 cells stably transfected with a PVPack-GP vector (containing gag and pol sequences) which was co-transfected with the plasmid pFB-Neo-lacZ and the vector PVPack-VSVG expressing vector, containing the G protein of the virus for vesicular stomatitis.

FIG. 17 shows that the transduced cells subsequently selected in the presence of puromycin all express the LacZ gene, as revealed in situ by β-galactosidase activity.

10. Expression of Oct-4, ABCG2 and Rex-1 in CA Stem Cells

Oct-4 is a transcription factor that is specifically expressed in mouse embryonic stem cells and is indispensable to maintaining their pluripotentiality. It has also been shown that Oct-4 is expressed by human embryonic stem cells.

The transcriptional expression of Oct-4 was demonstrated in the stem cells of the invention. RNA was extracted from CA cells (homogeneous populations and clonal populations) and Oct-4 expression was amplified by RT-PCR then detected by hybridization. The PCR conditions were: 94° C., 1 min; 57° C., 1 min; 72° C., 1 min for 45 cycles. –RT: negative control.

Similarly, transcriptional expression of ABCG2 was demonstrated in the stem cells of the invention. RNA was extracted from CA cells (homogeneous populations and clonal populations) and ABCG2 expression was amplified by RT-PCR then detected by hybridization. The PCR conditions for ABCG2 were: 94° C., 1 min; 60° C., 1 min; 72° C., 1 min for 31 cycles.

FIG. 18 shows the results obtained with Primo 2CA cells at transfer 16 (48 population doublings) and for cells of the Primo 2CA1 clone at transfer 5 (15 population doublings). They express Oct-4 and ABCG2.

Primo 2CA cells also express the transcription factor Rex-1 (FIG. 18, right hand side). The transcription factor Rex-1 is a specific marker for mouse and human embryonic stem cells. The PCR conditions for Rex-1 are as follows:

94° C. 1 min., 60° C. 1 min., 72° C. 1 min., number of cycles 31, 72° 5 min 1 cycle.

11. Characterization of CA Cells of the Invention in Terms of Surface Markers Characterization of the CA cells of the invention, particular of Primo 2CA cells, was further investigated in terms of surface markers using flow cytometry.

11.1. Methodology for Analyzing the Expression of Surface Markers by Flow Cytometry The labelling protocol was described above (see Example 7). The antibodies used were as follows:
HLA class I conjugated with fluorescein (FITC);
HLA-DR (HLA class II) conjugated with phycoerythrin (PE);
CD-3 (marker for T lymphocytes) conjugated with PE;
CD13 (marker for stromal cells of bone marrow, endothelial cells, early progenitors of granulocytes/monocytes and of their descendance) conjugated with FITC

11.2—Results of Characterization of CA Cells of the Invention in Terms of Surface Markers The Primo 2CA cells are surface negative for the expression of CD3, HLA class I and HLA-DR. In contrast, they are CD13 positive (marker expressed, inter alia, in bone marrow stromal cells (cf FIG. 20).

The absence of surface HLA class I and II molecules strongly suggests the non immunogenicity of Primo 2CA.

It is interesting to note that Primo 2CA cells differ from the human bone marrow cells described by Reyes et al (Blood, November 2001).

Those cells, termed MPC, for "Mesodermal Progenitor Cells" are HLA class I and class II negative and CD13 positive only when cultivated in low densities in a culture medium containing a low concentration of foetal calf serum (2%) with the obligatory presence of EGF and PDGF.

In contrast, cultivated in the presence of 10% foetal calf serum (concentration used to amplify the cells of the invention, in particular Primo 2CA cells), hMPCs display the inverse phenotype, namely HLA class I and HLA-DR positive and CD13 negative. The hMPCs, cultivated in the presence of 10% foetal calf serum or bFGF (FGF-2), lose their proliferation potential very rapidly and die.

12. In Vivo Differentiation of CA Stem Cells of the Invention into Endothelial Cells and into Myocytes Example 4 demonstrated that cells of the invention are capable of differentiating in vitro after three weeks into endothelial and cells and into myocytes.

The examples presented below demonstrate that the human CA cells of the invention (particular the cells of Primo 2CA, Primo 1CA and Primo 3CA) injected into the muscle of mdx mice, an animal model for Duchenne's disease in man, are capable of regenerating normal fibers after only 10 days. Surprisingly, said cells are not rejected when transplanted into the non immunosuppressed mouse. Said cells, by dint of their in vivo regeneration capacity and their absence of immunogenicity, offer a number of therapeutic perspectives in an allogenic context.

12.1 Transplantation Protocol and Analysis of In Vivo Regeneration by Immunofluorescence and FISH (Fluorescence in Situ Hybridization)

12.1.1. Transplantation Protocol

To analyse the in vivo regeneration potential of the CA cells of the invention (more particularly cells of Primo2 CA, Primo 1CA and Primo 3CA), the mdx mouse animal model (C57BL/10ScSn DMD$^{mdx}$/J), was used.

These mdx mice (X-chromosome—linked muscular dystrophy) constitute a good model for studying Duchenne myopathies in man as they have a point mutation of the gene for dystrophin (located on the X chromosome) causing non-translation of dystrophin. In man, the absence of dystrophin, a protein with a little known role, causes a cascade of events that are currently little understood, leading to the progressive disappearance of muscle fibers and death.

The following cells were used for the in vivo muscle regeneration experiments:
Primo 2CA cells obtained between 80 and 160 population doublings (more precisely 80, 120 and 160 population doublings);
Primo 1CA cells obtained at 50 and at 120 population doublings;
Primo 3CA cells at 45, 80 and 110 population doublings.

In all of the experiments 3 to 4 month old mdx mice of both genders were used.

The left Anterior Tibialis muscle was transplanted with 150 000 Primo 2CA, Primo 1CA or Primo 3CA cells taken up in a volume of 50 µl of HBSS (Hank's Buffered Saline solution). The same volume of HBSS was injected into the right muscle to serve as a negative control.

To analyse the muscle regeneration potential of the cells of the invention, in a first step we treated transplanted mice with an immunosuppressor, cyclosporin, to avoid the risk of immune rejection. The cyclosporine was administered intraperitoneally once a day in a concentration of 10 mg/kg of animal weight/day as of transplantation.

The transplanted mdx mice simultaneously treated with cyclosporine were sacrificed after 10 days.

In parallel, to test the non immunogenicity of Primo2 CA, Primo 1CA or Primo 3CA cells, the inventors used the same transplantation protocol but on mdx mice with a normal immune system, i.e. not treated with cyclosporine.

The transplanted muscles and the control muscles (injected only with 50 µl HBSS) were recovered and frozen in isopentane then liquid nitrogen.

12.1.2 Detection of Dystrophin by Immunofluorescence

12 µm seriated sections were prepared from the frozen and dehydrated muscles by successive passages of 10 minutes in 50, 75 and 100% ethanol.

To carry out dystrophin labeling, the frozen sections were fixed in methanol/glacial acetic acid (70/30, v/v) for 15 min at ambient temperature. After washing with PBS (phosphate buffered saline) and incubating for 30 min in a blocking solution (PBS+3% BSA (bovine serum albumin)), the sections were incubated for one hour with a specific antibody for human dystrophin (mouse anti-human IgG2a, Novocastra NCL-DYS3), or an antibody that recognized both human, rat and mouse dystrophin (mouse IgG1 NCL-DYS2, Novacastra). To reduce background noise, the antibody was first coupled with fluorescein (Alexa Fluor 488), using "Zenon Alexa Fluor 488 Mouse IgG2a or IgG1 Labeling Kit", depending on the antibodies (Molecular Probes).

The sections were then washed with PBS and then with water and analyzed using a fluorescence microscope (Olympus BH2).

12.1.3. Detection of Human Transplanted Nuclei by FISH (Fluorescence in situ Hybridization)

The slides were dehydrated by successive passages of 2 min in baths of ethanol in increasing concentrations (70, 80 and 100%), then denatured at 73° C. in a 70% formamide/2× SSC solution (citrated saline solution) for 2 min 30 s. The slides were then rehydrated (ethanol baths in decreasing concentrations of 100, 80 and 70%) before proceeding to hybridization.

The probe used to detect human nuclei was a specific probe for all human centromers (α-Satellite) coupled with digoxigenin (CP5095-DG.5, Appligene Oncor).

The probe, initially dilated in the hybridization buffer Hybrisol VI (Appligene Oncor) (1 µl of probe for 10 µl of buffer), was denatured for 5 min at 72° C. then deposited on the slides. The hybridization step was carried out at 37° C. in a moist chamber for 12 h.

The slides were then washed: 1 wash in 50% formamide/2×SSC at 43° C. for 15 min followed by washing in 2×SSC at 37° C. for 8 minutes.

The final step was a detection step consisting of applying to the slides an anti-digoxigenin antibody coupled with rhodamine (Appligene Oncor) (5 min in the dark).

Before analyzing the sections, the nuclei were stained completely using a DAPI solution (blue stain).

The slides were then observed under a fluorescence microscope (Axiophot Zeiss) with a 100 watt lamp and a filter system (Perceptive Scientific International).

12.1.4. Double Immunofluorescence Labeling/FISH

In order to co-localize human nuclei with muscle fibers re-expressing dystrophin, the inventors carried out double labeling (dystrophin/human nuclei). To this end, the dystrophin detection step was carried out before labeling the human nuclei by FISH.

12.2—Results: Muscle Regeneration Capacity and Non Immunogenicity of CA Cells of the Invention In Vivo

12.2.1 Muscle Regeneration Capacity In Vivo

Many studies regarding the multipotentiality of adult stem cells in vivo have been questioned, in particular after demonstrating the fusion power of said cells (Terada et al, Nature 2002; Wurmser et al, Nature, 2002 and Ying et al, Nature, 2002). Further, certain studies suggest that the capacity of said cells to express specific markers for the tissue into which they have been transplanted is an extremely rare event (Wagers et al, Science, 2002; Morshead et al, Nature, 2002).

To avoid the problems mentioned above, mdx mice, an animal model for Duchenne's disease, were used. These mice are deficient in dystrophin (a point mutation in the gene). (In reality, there exists a small number of reverting fibers that re-express dystrophin but the percentage of those fibers does not exceed 1% (Hoffman et al., J Neurol Sci, 1990; Gillis, J Muscle Research and Cell Motility, 1999)).

Firstly, to avoid any rejection problems, the mdx mice were treated with an immunosuppressor, cyclosporin.

Injection of a small number of Primo 2CA cells (100000 to 150000 cells) into the Tibialis Anterior muscle resulted in restoration of dystrophin in about 50% of the fibers in only 10 days. These positive fibers were collected in clusters (corresponding to the injection point).

In agreement with the above results, using FISH, human nuclei with muscle fibers positive for dystrophin (cf FIGS. 24 and 25) could be located.

Similar results were obtained for Primo 2CA cells between 60 and 160 population doublings, treated or not treated with bFGF (FGF-2). Similar results were obtained with the CA1 clone derived from the Primo 2CA population.

12.2.2 Non Immunogenicity of CA Cells In Vivo

In contrast to the majority of somatic cells, the CA cells of the invention are free of HLA class I markers (see Example 7) and surface HLA class II markers (Example 11). This extremely rare phenotype strongly suggests the non-immunogenicity of the CA cells of the invention.

To validate the non-immunogenicity of these cells in vivo, an experimental approach similar to that described in section 12.2.1 was used, except that non immunosuppressed mdx mice were used.

After 10 days of transplantation, the muscle of the transplanted and non-immunouppressed mice re-expresses dystrophin levels comparable with that of mice treated with cyclosporin. A muscle regeneration potential was observed, both for Primo 2CA cells and for Primo 1CA cells and Primo 3CA cells in the absence of an immunosuppressor (see FIG. 24 for Primo 2CA cells and FIG. 31 for Primo 1CA cells and Primo 3CA cells).

After 50 days of transplantation, in the absence of immunosuppressor, the number of muscle fibers positive for dystrophin continued to increase in the injected Tibialis Anterior but fibers were also found in other muscles such as the gastrocnemius (cf FIG. 25). These results strongly suggest that Primo 2CA cells are capable not only of regenerating muscle at the injection point but also of migrating to repair the surrounding muscles. An increase in the percentage of peripheral nuclei of human origin within the fibers and a reduction in the percentage of central nuclei was observed 10 to 50 days after transplantation (73% a 85%, and 27% a 15% respectively), indicating that the injected cells participate in terminal differentiation of myocytes.

Using FISH, the human nuclei were still present and co-localised with the dystrophin-positive fibers. Further, the localization of a certain number of human nuclei at the outer periphery of the positive fibers suggests the presence of human satellite cells and/or of endothelial cells of human origin.

By comparison, transplantation of a large quantity of human myoblasts (4 million) into non-immunosuppressed mice resulted in complete rejection after one month (Huard et al, Muscle and Nerve, 1994) and thus no muscle regeneration.

After 80 days transplantation, the number of muscle fibers positive for dystrophin continued to increase in the injected muscle, and fibers were still found in the gastrocnemius cf FIG. 26).

After 6 months transplantation, more than 80% of the fibers expressed human dystrophin as opposed to 50% at earlier times (FIG. 27). Further, within the fiber, we determined much more regular expression of dystrophin compared with earlier transplantation times in which dystrophin expression was irregular in the same fiber. Further, the transplanted muscle exhibited a substantial improvement in fiber morphology (more regular and an absence of necrosis, an important process in mdx mice of this age).

These observations indicate that the transplanted cells do not give rise to any rejection reaction in the immunocompetent mouse. The non-immunogenic nature of the transplanted cells has been demonstrated using hematoxylin stain. No rejection reaction (absence of infiltration by CD3+ T lymphocytes) was observed after 10 days (FIG. 29), 50 days, 80 days (results not shown) or after 6 months transplantation of Primo 2CA cells (see FIG. 30). Similarly, the absence of lymphocyte infiltration could also be observed 10 days after transplantation of Primo 1CA and Primo 3CA cells, confirming the absence of a rejection reaction. The same results were obtained with Primo 1CA cells. The immunoprivileged behavior of Primo 1CA cells and Primo 3CA cells was thus identical to that observed with Primo 2CA. These results were also confirmed using an anti-CD3 antibody, demonstrating the absence of lymphocyte infiltration.

In contrast, transplantation of unpurified human stromal-vascular cells isolated from human adipose tissue induced a cytotoxic and humoral immune reaction (FIGS. 29(c) and (c')).

In conclusion, after six months transplantation, the cells caused a substantial improvement in the transplanted muscle with a high percentage of fibers expressing human dystrophin and an absence of necrosis which is observed in untreated mdx mice of the same age; this was in the absence of an immunosuppressor.

The human origin of the dystrophin expressed in the myofibers of the transplanted muscle has been demonstrated by comparative immunodetection, using an antibody specific for human dystrophin (directed against the N-terminal end of human dystrophin: mouse anti-human IgG2a: NCL-DYS3 from Novocastra,), and an antibody capable of recognizing both human dystrophin and murine dystrophin (directed against the C-terminal end of human and murine dystrophin: mouse anti-human IgG1: NCL-DYS2 from Novocastra,).

The results of this comparative immunodetection are shown in FIG. 28. The presence of myofibers expressing dystrophin and the subcellular location in the Tibialis Anterior 10 days after transplantation is visible. The similarity between FIGS. 28(*a*) and (*b*) indicates the human origin of the expressed dystrophin. The human dystrophin is located beneath the sarcolemma. In contrast, mouse collagen III is present in the extracellular space between the myofibers (FIGS. 28(*c*) to (*e*)).

The mechanisms involved in the tolerance of the CA cells of the invention in a xenogenic context, i.e. in an organism that is immunologically very different (mdx mouse) still have to be elucidated.

However, it may be supposed that a certain number of cells located at the outer periphery of the muscle fibers play a key role in this tolerance. These cells may play a local immunosuppression role by synthesizing immunosuppressive factors, for example anti-inflammatory type Th2 cytokines such as IL10 and/or by expressing surface proteins leading to the absence of recognition by alloreactive lymphocytes of the host (Jorgensen et al, Engineering mesenchymal stem cells for immunotherapy, Gene Therapy 10, 928-931 (2003)).

These cells can also induce generalized tolerance by re-educating the host's immune system. The presence of human CA cells in the thymus and spleen of the host reinforces this hypothesis (Fändrich F et al, "Preimplantation-stage stem cells induce long-term allogeneic graft acceptance without supplementary host conditioning", Nat. Med 8, 171-178 (2002).

These results demonstrate the immunoprivilege of the human CA cells of the invention which are capable of regenerating muscle without being rejected. These cells thus offer many prospects for cell therapies in allotransplantation. In particular, for genetic diseases such as myopathies where autotransplantations are impossible, the use of cells similar to Primo 2CA would constitute a good therapeutic alternative.

The invention claimed is:

1. A cell population consisting essentially of adult multipotent human stem cells, which cell population is either quiescent or is proliferating in the undifferentiated state, and requires growth factor to proliferate beyond 70% confluence, and wherein each of said adult multipotent human stem cell has a capacity for self-renewal preserved for at least 130 population doublings, and stably exhibits the following phenotype in vitro:
   HLA Class I negative,
   an endogenous telomerase activity of at least 20% of the telomerase activity of the HEK293T transformed cell line,
   a normal karyotype, and
   a degree of senescence of less than 0.05% at 60 population doublings.

2. The cell population of claim 1, wherein the cell population is clonal.

3. The cell population of claim 1, wherein the cell population requires the presence of basic fibroblast growth factor (bFGF) to proliferate beyond 70% confluence.

4. The cell population according to claim 1, wherein each of said adult multipotent human stem cells stably exhibits the following phenotype in vitro at quiescence:
   HLA class I negative,
   HLA class II negative,
   CD3 negative,
   CD13 positive,
   LIF-R negative,
   Oct-4 positive,
   Rex-1 positive,
   ABCG2 positive.

5. The cell population of claim 1, wherein the cell has immunoprivileged behavior in vivo and a capacity to migrate in the undifferentiated state.

6. The cell population according to claim 1, wherein each of said adult multipotent human stem cells has a self-renewal capacity preserved for at least 200 population doublings.

7. The cell population according to claim 1, wherein said cell population can be isolated from human adipose tissue.

8. The cell population according to claim 1, wherein each of said adult multipotent human stem cells can differentiate into a cell of endodermal, ectodermal or mesodermal origin.

9. The cell population according to claim 8, wherein each of said adult multipotent human stem cells is capable of differentiating into an adipocyte, osteoblast, myocyte, chondrocyte or endothelial cell.

10. A cosmetic composition comprising the cell population according to claim 1, and an excipient, vehicle, solvent, colorant, fragrance, antibiotic or additive suitable for use in a cosmetic product.

* * * * *

UNITED STATES PATENT AND TRADEMARK OFFICE
CERTIFICATE OF CORRECTION

| | | |
|---|---|---|
| PATENT NO. | : 8,334,135 B2 | Page 1 of 1 |
| APPLICATION NO. | : 10/632581 | |
| DATED | : December 18, 2012 | |
| INVENTOR(S) | : Rodriguez et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 515 days.

Signed and Sealed this
Twenty-third Day of December, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,334,135 B2 | Page 1 of 1 |
| APPLICATION NO. | : 10/632581 | |
| DATED | : December 18, 2012 | |
| INVENTOR(S) | : Rodriguez et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 790 days.

Signed and Sealed this
Nineteenth Day of May, 2015

Michelle K. Lee
*Director of the United States Patent and Trademark Office*

SEQUENCE LISTING

```
<160> NUMBER OF SEQ ID NOS: 8

<210> SEQ ID NO 1
<211> LENGTH: 25
<212> TYPE: DNA
<213> ORGANISM: artificial sequence
<220> FEATURE:
<223> OTHER INFORMATION: primer

<400> SEQUENCE: 1
gacaacaatg aaaatcttca ggaga                                              25

<210> SEQ ID NO 2
<211> LENGTH: 23
<212> TYPE: DNA
<213> ORGANISM: artificial sequence
<220> FEATURE:
<223> OTHER INFORMATION: primer

<400> SEQUENCE: 2
ttctggcgcc ggttacagaa cca                                                23

<210> SEQ ID NO 3
<211> LENGTH: 20
<212> TYPE: DNA
<213> ORGANISM: artificial sequence
<220> FEATURE:
<223> OTHER INFORMATION: primer

<400> SEQUENCE: 3
cactcggttc tcgatactgg                                                    20

<210> SEQ ID NO 4
<211> LENGTH: 20
<212> TYPE: DNA
<213> ORGANISM: artificial sequence
<220> FEATURE:
<223> OTHER INFORMATION: primer

<400> SEQUENCE: 4
ggcctcagga agacttatgt                                                    20

<210> SEQ ID NO 5
<211> LENGTH: 20
<212> TYPE: DNA
<213> ORGANISM: artificial sequence
<220> FEATURE:
<223> OTHER INFORMATION: primer
```

```
<400> SEQUENCE: 5
aaggaggtgg tgtagctgat                                              20

<210> SEQ ID NO 6
<211> LENGTH: 19
<212> TYPE: DNA
<213> ORGANISM: artificial sequence
<220> FEATURE:
<223> OTHER INFORMATION: primer

<400> SEQUENCE: 6
ctctccagta tgaaccagg                                               19

<210> SEQ ID NO 7
<211> LENGTH: 20
<212> TYPE: DNA
<213> ORGANISM: artificial sequence
<220> FEATURE:
<223> OTHER INFORMATION: primer

<400> SEQUENCE: 7
gaaaggatca gaacaacagc                                              20

<210> SEQ ID NO 8
<211> LENGTH: 20
<212> TYPE: DNA
<213> ORGANISM: artificial sequence
<220> FEATURE:
<223> OTHER INFORMATION: primer

<400> SEQUENCE: 8
ggcattgacc tatcagatcc                                              20
```